(12) United States Patent
Colosimo et al.

(10) Patent No.: US 10,527,570 B2
(45) Date of Patent: Jan. 7, 2020

(54) DETERMINING LOCATION OF ELECTROMAGNETIC IMPEDANCE SPECTROGRAPHIC ANALYSIS USING ELECTROMAGNETIC IMPEDANCE TOMOGRAPHY

(71) Applicant: TransTech Systems, Inc., Latham, NY (US)

(72) Inventors: Donald D. Colosimo, Saratoga Springs, NY (US); Sarah E. Pluta, Scotia, NY (US); John W. Hewitt, Niskayuna, NY (US)

(73) Assignee: TRANSTECH SYSTEMS, INC., Latham, NY (US)

(*) Notice: Subject to any disclaimer, the term of this patent is extended or adjusted under 35 U.S.C. 154(b) by 333 days.

(21) Appl. No.: 15/403,523

(22) Filed: Jan. 11, 2017

(65) Prior Publication Data
US 2017/0199140 A1   Jul. 13, 2017

Related U.S. Application Data

(60) Provisional application No. 62/277,690, filed on Jan. 12, 2016.

(51) Int. Cl.
*G01N 27/02* (2006.01)
(52) U.S. Cl.
CPC .................. *G01N 27/026* (2013.01)
(58) Field of Classification Search
CPC ...................................................... G01N 27/026
See application file for complete search history.

(56) References Cited

U.S. PATENT DOCUMENTS 2,240,520 A    5/1941   Schlumberger
2,264,725 A   12/1941   Shoupp et al.
(Continued)

FOREIGN PATENT DOCUMENTS

WO    2010144313 A2   12/2010

OTHER PUBLICATIONS

Li et al., The Physical Modeling Experiments Analysis of the Exploration Depth of Conventional Electric Survey, PIERS Proceedings, Symposium, Mar. 22-26, 2010, School of Info—physics and Geometrics Engineering, Changsha, China.
(Continued)

*Primary Examiner* — Hyun D Park
(74) *Attorney, Agent, or Firm* — Hoffman Warnick LLC

(57) ABSTRACT

Approaches include selecting a desired location for the measurement of electromagnetic spectroscopic impedance data for correlation with a physical property of a material under test (MUT) with electromagnetic impedance tomography. The MUT is first characterized tomographically with a series of four-terminal electrode patterns at a single current frequency. Measured and computed values of electromagnetic impedance for the voxels and sub-voxels of the MUT are determined. The sub-voxel with a targeted value of impedance is selected and matched with the specific four-terminal electrode pattern related to that sub-voxel. The spectrographic electromagnetic impedance measurements are made across a range of frequencies for the selected sub-voxel, using all of the four-terminal electrode patterns required to compute the tomographic impedance value of the selected sub-voxel. The computed spectrographic electromagnetic impedance value for the selected sub-voxel is then correlated to a physical property of the MUT.

8 Claims, 19 Drawing Sheets

(56) References Cited

U.S. PATENT DOCUMENTS

| | | | |
|---|---|---|---|
| 4,979,197 | A | 12/1990 | Troxler, Sr. et al. |
| 5,099,504 | A | 3/1992 | Pettit |
| 5,272,624 | A | 12/1993 | Gisser et al. |
| 5,381,333 | A | 1/1995 | Isaacson et al. |
| 5,544,662 | A | 8/1996 | Saulnier et al. |
| 5,890,489 | A | 4/1999 | Elden |
| 5,900,736 | A | 5/1999 | Sovik et al. |
| 6,380,745 | B1 | 4/2002 | Anderson et al. |
| 6,400,161 | B1 | 6/2002 | Geisel |
| 6,414,497 | B1 | 7/2002 | Sovik et al. |
| 6,677,763 | B2 | 1/2004 | Geisel |
| 6,703,847 | B2 | 3/2004 | Venter et al. |
| 7,040,145 | B2 | 5/2006 | Drnevich et al. |
| 7,068,050 | B2 | 6/2006 | Steele et al. |
| 7,219,021 | B2 | 5/2007 | Liu et al. |
| 7,289,916 | B2 | 10/2007 | Drnevich et al. |
| 7,701,227 | B2 | 4/2010 | Saulnier et al. |
| 8,011,248 | B2 | 9/2011 | Troxler |
| 2002/0032531 | A1 | 3/2002 | Mansky et al. |
| 2005/0267700 | A1 | 12/2005 | Gamache et al. |
| 2009/0270756 | A1 | 10/2009 | Gamache et al. |
| 2010/0039125 | A1 | 2/2010 | Buchler |
| 2010/0268041 | A1* | 10/2010 | Kraemer ............ A61B 5/0537 600/301 |
| 2011/0230746 | A1* | 9/2011 | Jarverud ............ A61N 1/3627 600/374 |
| 2012/0013354 | A1 | 1/2012 | Bowler et al. |
| 2012/0130212 | A1 | 5/2012 | Pluta et al. |
| 2013/0307564 | A1* | 11/2013 | Colosimo ............ G01R 27/06 324/647 |
| 2015/0212026 | A1 | 7/2015 | Pluta et al. |

OTHER PUBLICATIONS

Saulnier et al., An Electrical Impedance Spectroscopy System for Breast Cancer Detection, Engineering in Medicine and Biology Society, Symposium, Aug. 22-26, 2007, p. 4154-4157, Annual International Conference of the IEEE, Troy, NY, USA.

Alumbaugh et al., A Hybrid Hydrologic—Geophysical Inverse Technique for the Assessment and Monitoring of Leachates in the Vadose Zone, Sandia National Laboratories, p. 1-26, Department of Energy, USA.

Roth et al., Calibration of Time Domain Reflectometry for Water Content measurement Using a Composite Dielectric Approach, Journal, Oct. 1990, p. 2267-2273, vol. 26 No. 10, Water Resources Research.

Nyfors et al., Industrial Microwave Senors, Journal, 1991, p. 1009-1012, CH. 2870, IEEE.

Neithalath et al., Characterizing Enhanced Porosity Concrete using Electrical Impedance to Predict Acoustic and Hydraulic Performance, Journal, p. 1-39, Clarkson University.

Loke, Electrical Imaging Surveys for Environmental and Engineering Studies, Guide, Aug. 1999, Malaysia.

Kulkarni et al., A Two-Layered Forward Model of Tissue for Electrical Impedance Tomography, Manuscript, Jun. 2009, p. 1-24, Physiol Meas. USA.

Kulkarni et al., An Analytical Layered Forward Model for Breasts in Electrical Impedance Tomography, Manuscript, Jun. 2008, p. 1-22, Physiol Meas PMC 2008, USA.

Hilhorst, Dielectric Characterisation of Soil, Book, 1998, p. 1-141, Institute of Agricultural and Environmental Engineering, Wageningen, NE.

Dvorak, FEA Software Ready to Model Many Physical Phenomena, Article, Jul. 8, 2004, p. 1-5, Machine Design, USA.

Gamache, Electromagnetic Material Properties Sensor, Symposium, 2005, p. 1-6, Proceedings of the COMSOL Multiphysics User's Conference, Boston, USA.

Gamache, Development of an In-Process Soil Compaction Measurement Instrument, Report, Mar. 2004, p. S1-8-6, The New York State Energy Research and Development Authority, Schenectady, NY. USA.

Gamache, A Comparison of FDFD and FEM Methods Applied to the Buried Mine Problem, Article, p. 1-7, TransTech Systems,Inc., Schenectady, NY, USA.

El-Shenawee et al., Spherical Harmonics Microwave Algorithm for Shape and Location Reconstruction of Breast Cancer Tumor, Journal, Oct. 2006, p. 1258-1271, vol. 25, IEEE Transactions on Medical Imaging.

Laurent et al., Echographic Measurement of Skin Thickness in Adults by High Frequency Ultrasound to Assess the Appropriate Microneedle Length for Intradermal Delivery of Vaccines, Jun. 2007, p. 6423-6430, vol. 25, Vaccine.

Dahlin et al., Combined Resistivity Imaging and RCPT for Geotechnical Pre-investigation, Journal, 2004, p. 1-9, Procs. NGM 2004, Ystad, Sweden.

Cornean et al., Towards a D-Bar Reconstruction Method for Three-Dimensional EIT, Article, p. 1-19, Aalborg University, DE.

Charbonnier et al. , Deterministic Edge-Preserving Regularization in Computed Imaging, Journal, Feb. 1997, p. 298-311, vol. 6 No. 2, IEEE Transactions on Image Processing.

Birchak, High Dielectric Constant, Microwave Probes for Sensing Soil Moisture, Journal, Jun. 28, 2005, p. 93-98, vol. 62 Issue 1, Proceedings of the IEEE.

Belge et al., Wavelet Domain Image Restoration with Adaptive Edge-Preserving Regularization, Journal, Aug. 5, 1999, p. 1-32, IEEE Transactions on Image Processing.

* cited by examiner

DETERMINING LOCATION OF ELECTROMAGNETIC IMPEDANCE SPECTROGRAPHIC ANALYSIS USING ELECTROMAGNETIC IMPEDANCE TOMOGRAPHY

CROSS-REFERENCE TO RELATED APPLICATIONS

This application claims priority to U.S. Provisional Patent Application No. 62/277,690, filed on Jan. 12, 2016, which is hereby incorporated by reference in its entirety.

TECHNICAL FIELD

Various aspects of the disclosure relate to selecting a location for electromagnetic impedance spectrographic (EMIS) characterizations of specific volumes beneath the surface of a material under test (MUT) using electromagnetic impedance tomography (EMIT), e.g., with a four-terminal electrode array.

BACKGROUND

The use of electromagnetic tomographic and spectrographic measurement devices have been identified in US Patent Publications 2013/0307564 and 2015/0137831 and U.S. Provisional Patent Application Nos. 61/703,488 and 61/932,400 (each of which is hereby incorporated by reference in its entirety) to locate specified volumes within a material under test (MUT), and to characterize that volume based upon its electromagnetic characteristics using two-terminal sensor arrays. A two-terminal sensor array consists of a positive and negative electrode pair conducting either a current or voltage signal through the MUT. The electrode configuration may consist of a single positive (transmitting) electrode and multiple negative (receiving) electrodes, where the single transmitting electrode and each of the receiving electrodes constitute a pair. In US Patent Publication 2012/0130212 (hereby incorporated by reference in its entirety), a four-terminal sensor array is presented to measure blood metabolite levels. Where the location of the spectroscopy measurement can be selected such that the signal has desired or target impedance properties, the data and resulting conclusions may be useful. For example, where the desire is to measure blood metabolites, the area selected for measurement should have the greatest volume of blood in the measurement area.

SUMMARY

Aspects of the invention include systems and approaches for securing the electromagnetic impedance characteristics of selected volumes of materials under test using four-terminal measurements. In some embodiments, a system is disclosed including: at least one computing device configured to characterize a physical property of a material under test (MUT) by performing actions including: instructing a sensor system to transmit a plurality of electromagnetic impedance signals into the MUT from a surface of the MUT; obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT; comparing each of the plurality of sets of return electromagnetic impedance readings with a data set representing an expected impedance response of the MUT; calculating the physical property of the MUT using one of the plurality of sets of return electromagnetic impedance readings differing from a mean of the data set representing an expected impedance response of the MUT; and determining the physical property of a selected sub-volume of the MUT based upon the set of return electromagnetic impedance readings differing from the mean and a physical relationship between distinct sub-volumes of the MUT.

A first aspect of the disclosure includes: a system having: at least one computing device configured to characterize a physical property of a material under test (MUT) by performing actions including: instructing a sensor system to transmit a plurality of electromagnetic impedance signals into the MUT from a surface of the MUT; obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT; comparing each of the plurality of sets of return electromagnetic impedance readings with a data set representing an expected impedance response of the MUT; calculating the physical property of the MUT using one of the plurality of sets of return electromagnetic impedance readings differing from a mean of the data set representing an expected impedance response of the MUT; and determining the physical property of a selected sub-volume of the MUT based upon the set of return electromagnetic impedance readings differing from the mean and a physical relationship between distinct sub-volumes of the MUT.

A second aspect of the disclosure includes: a computer-implemented method of characterizing a physical property of a material under test (MUT), performed using at least one computing device, the method including: instructing a sensor system to transmit a plurality of electromagnetic impedance signals into the MUT from a surface of the MUT; obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT; comparing each of the plurality of sets of return electromagnetic impedance readings with a data set representing an expected impedance response of the MUT; calculating the physical property of the MUT using one of the plurality of sets of return electromagnetic impedance readings differing from a mean of the data set representing an expected impedance response of the MUT; and determining the physical property of a selected sub-volume of the MUT based upon the set of return electromagnetic impedance readings differing from the mean and a physical relationship between distinct sub-volumes of the MUT.

A third aspect of the disclosure includes: a computer program product having program code stored on a computer-readable storage medium, which when executed by at least one computing device, causes the at least one computing device to characterize a physical property of a material under test (MUT) by performing actions including: instructing a sensor system to transmit a plurality of electromagnetic impedance signals into the MUT from a surface of the MUT; obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT; comparing each of the plurality of sets of return electromagnetic impedance readings with a data set representing an expected impedance response of the MUT; calculating the physical property of the MUT using one of the plurality of sets of return electromagnetic impedance readings differing from a mean of the data set representing an expected impedance response of the MUT; and determining the physical property of a selected sub-volume of the MUT based upon the set of return electromagnetic impedance readings differing from the mean and a physical relationship between distinct sub-volumes of the MUT.

DETAILED DESCRIPTION

Figure 1:
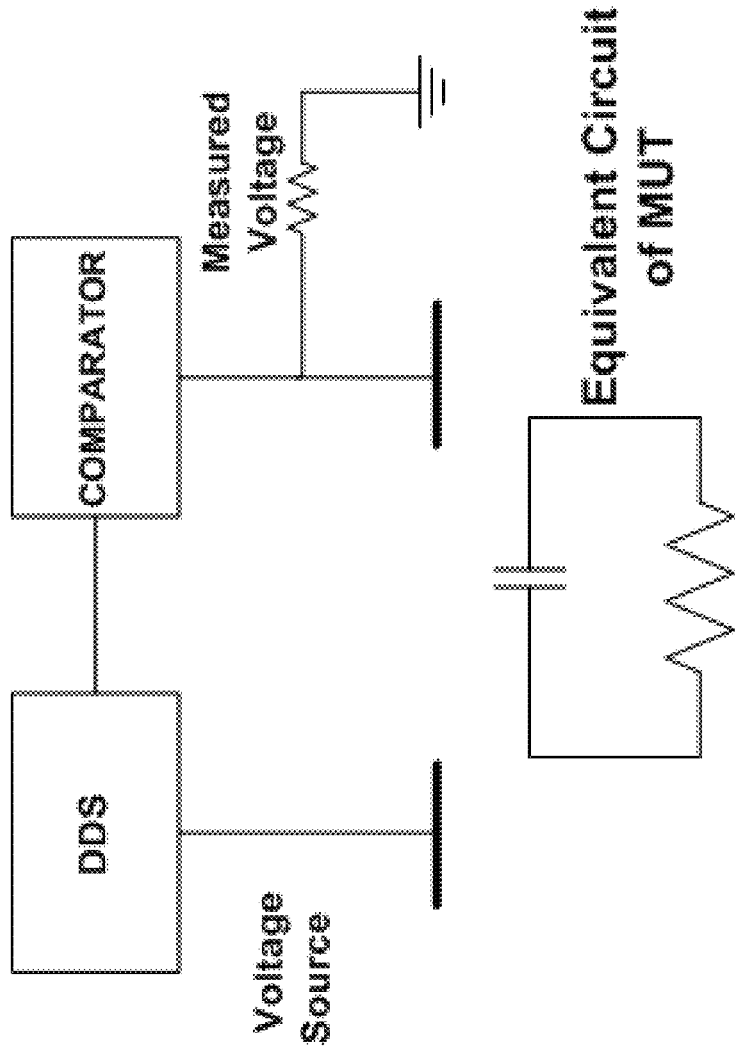
FIG. 1 is an illustration of a two-terminal measurement system according to the prior art.

Various aspects of the disclosure include approaches which expand on and improve conventional approaches for converting the measured impedance of volumes of material into the calculated impedance in sub-volumes. This methodology is termed Volume Differentiation and Removal (VDR). The term "voxel" is used to refer to "volume pixels", which are the electrical properties of a volume of the material under test (MUT) in which the impedance is directly measured. The term "sub-voxel" is used to denote the sub-volume of the MUT in which the impedance is computed from the measured values of impedance in the voxel.

The electromagnetic impedance characteristics of blood are significantly different than those of skin tissue. Various aspects of the disclosure present approaches for identifying a volume of tissue (e.g., human tissue), both horizontally (e.g. across the surface of the skin) and vertically (e.g. into the tissue), that has desired impedance values using tomographic methods. As whole blood is about ten-times more conductive than fat, various approaches aim to analyze the maximum impedance values observed. In various cases, a method involves arranging electrode patterns and configurations with a four-terminal sensor array system to secure single frequency data for a tomographic model of skin tissue and/or blood. That single-frequency data can be used to determine characteristics of the skin tissue and/or blood.

In various embodiments, approaches include determining tomographic and spectrographic characteristics for selected sub-volumes of an MUT using a tomography model and an equivalent circuit model with inputs from actual measurements obtained from various volumes of the MUT. Various embodiments include a system having an electrode array that allows for selection of particular electrodes to probe distinct sub-volumes of the MUT.

In various embodiments, the total number of electrodes in the array allow for repetitive data collection over a measurement area. While various aspects of the disclosure focus on a one-dimensional linear electrode array, a similar approach may be used on a two-dimensional planar electrode array.

Embodiments include a method and apparatus having of various electrode sensor array configurations incorporated into systems configured to communicate with various materials under test. As described in the prior referenced art, the system(s) can include: a signal generator operably connected with the array of electrodes, the signal generator for transmitting oscillating electromagnetic field signals through the array of electrodes at a range of selected frequencies; a signal detector operatively connected to the array of electrodes, the array of electrodes in communication with the material under test; a signal comparator operatively connected to the signal generator and the signal detector; and at least one computing device operably connected with the signal comparator. The at least one computing device is configured to determine a desired MUT volume with electromagnetic impedance tomography so that electromagnetic impedance spectrographic characteristics of the selected volume of the MUT may be determined. The at least one computing device may also be configured to correlate the electromagnetic impedance spectrographic characteristics of selected volumes of the MUT to physical properties of those volumes. The at least one computing device may also provide output to the user in various formats and transfer data files to another computer by various means.

According to various embodiments shown and described herein, electromagnetic impedance spectrographic characteristics of selected volumes of the MUT can be obtained by forming electrically conductive communication (contacting) between a four-terminal sensor array (e.g., linear sensor array, or set of linear sensor arrays forming a planar sensor array) and the MUT. In some cases, however, direct contact with the MUT may not be necessary, for example, where a spacing between the sensor array and the MUT can be accounted for in correlating impedance readings with expected responses for particular materials.

Various embodiments include approaches for characterizing a physical property of a material under test (MUT) by performing actions including: instructing a sensor system to transmit a plurality of electromagnetic impedance signals into the MUT from a surface of the MUT; obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT; comparing each of the plurality of sets of return electromagnetic impedance readings with a data set representing an expected impedance response of the MUT; calculating the physical property of the MUT using one of the plurality of sets of return electromagnetic impedance readings differing from a mean of the data set representing an expected impedance response of the MUT; and determining the physical property of a selected sub-volume of the MUT based upon the set of return electromagnetic impedance readings differing from the mean and a physical relationship between distinct sub-volumes of the MUT.

It is understood that each material that is placed under test and inspection (e.g., each MUT) has unique impedance characteristics which are taken into account in calibrating approaches according to various aspects of the invention. These included the "expected impedance response" that affect the sizing and spacing of the electrode array, the frequency used for tomographic probing, the frequency range for spectrographic analysis, and the method(s) used to correlate the measured impedance with the physical property of interest. Aspects of the disclosure used to locate and characterize a physical property in a blood sample in tissue will be different from those used to characterize other materials, e.g., the density and moisture content of a soil.

Some approaches include a system including: an array of electrodes for communicating with a surface and a subsurface volume; a signal generator operably connected with the array of electrodes; and at least one computing device operably connected with the signal generator and the array of electrodes, the at least one computing device configured to: instruct the signal generator to transmit a first set of single frequency signals (e.g., at a selected frequency) from the first pattern of electrodes into the surface and the subsurface; obtain an impedance measurement from the first pattern of electrodes; instruct the signal generator to transmit a second set of single frequency signals (e.g., at the selected frequency) from the second pattern of electrodes into the surface and the subsurface; obtain an impedance measurement from the second pattern of electrodes; repeat this process for all the patterns of electrodes required to provide the tomographic model with the measurements necessary to compute the sub-voxels from the measured voxels; select the desired sub-voxel by identifying the sub-voxel that matches the selection criteria; instruct the signal generator to transmit a series of signals to secure a spectrographic measurement over a selected range of frequencies from the electrode patterns that permit the computation of the spectrographic impedance values of the selected sub-voxel; and apply the spectrographic impedance physical property from the sub-voxel to characterize a characteristic property of the MUT (e.g., the tissue or blood).

Specific design strategies and approaches will be disclosed to be able to apply tomographic methods to identify regions of interest and to isolate the impedance characteristics of specific volumes of the MUT. A four-terminal array consists of two electrodes transmitting a current and two electrodes measuring a voltage induced by the current flow. The design of the sensor array and the configuration of the electrode patterns in the array is such that data is secured in a fashion to permit the selection by tomography of volumes of the MUT at varying depths and locations in order that the spectrographic characterization of the electromagnetic properties of the material within that selected volume may be optimized within the area and volumes being measured. The electromagnetic impedance spectrographic data may then be related to a physical attribute of the MUT by applying a correlation algorithm. The correlation algorithm relating an electromagnetic impedance feature to the physical attribute may be determined by any number of well-known correlation methods, such as, analysis of variations (ANOVA), neural networks, multiple regressions, look-up table(s), or any other such methods that correlate a specific electromagnetic impedance value with a value of the desired physical attribute that is measured or determined by a generally accepted method.

According to various embodiments, a MUT can include any material capable of being characterized via one or more approaches shown and/or described herein. In various embodiments, a MUT includes a mineral or organic material such as a soil, or a biological material such as tissue, sub-tissue, organs, fluids, etc. A MUT can include synthetic, composite and/or other blended/modified materials. A MUT can also include elemental materials, as well as materials including impurities. It is understood that the teachings described according to the various embodiments herein can be applied to any MUT described herein, as well as other materials that can be characterized according to the approaches of the various embodiments.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely illustrative.

Illustrations with respect to one or more implementations, alterations and/or modifications can be made to the illustrated examples without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

U.S. Pat. Nos. 5,900,736; 6,400,161; 6,414,497; and 6,677,763 (each of which is hereby incorporated by reference in its entirety) present a two electrode sensor array as a means to evaluate the density of asphalt using electromagnetic impedance characteristics of the asphalt. This concentric two or three electrode sensor using a two-terminal measurement may also be classified electrically as a coplanar wave guide. This prior art does not use any spectrographic or tomographic approaches but illustrates two electrode geometries for use with electromagnetic impedance measuring devices. U.S. Pat. No. 7,219,021 (hereby incorporated by reference in its entirety) presents the use of electromagnetic impedance spectroscopy to evaluate the density and moisture of soils with electrode geometry similar to that in U.S. Pat. Nos. 5,900,736 and 6,414,497. These electrode arrays are in non-conductive communication with the MUT. U.S. Provisional Patent Application Nos. 61/647,848 and 61/703,488 (each of which is hereby incorporated by reference in its entirety) present two different methods of evaluating a MUT with impedance spectroscopy and impedance tomography with linear electrode arrays using a two-terminal measurement in non-conductive communication the MUT.

Figure 2:
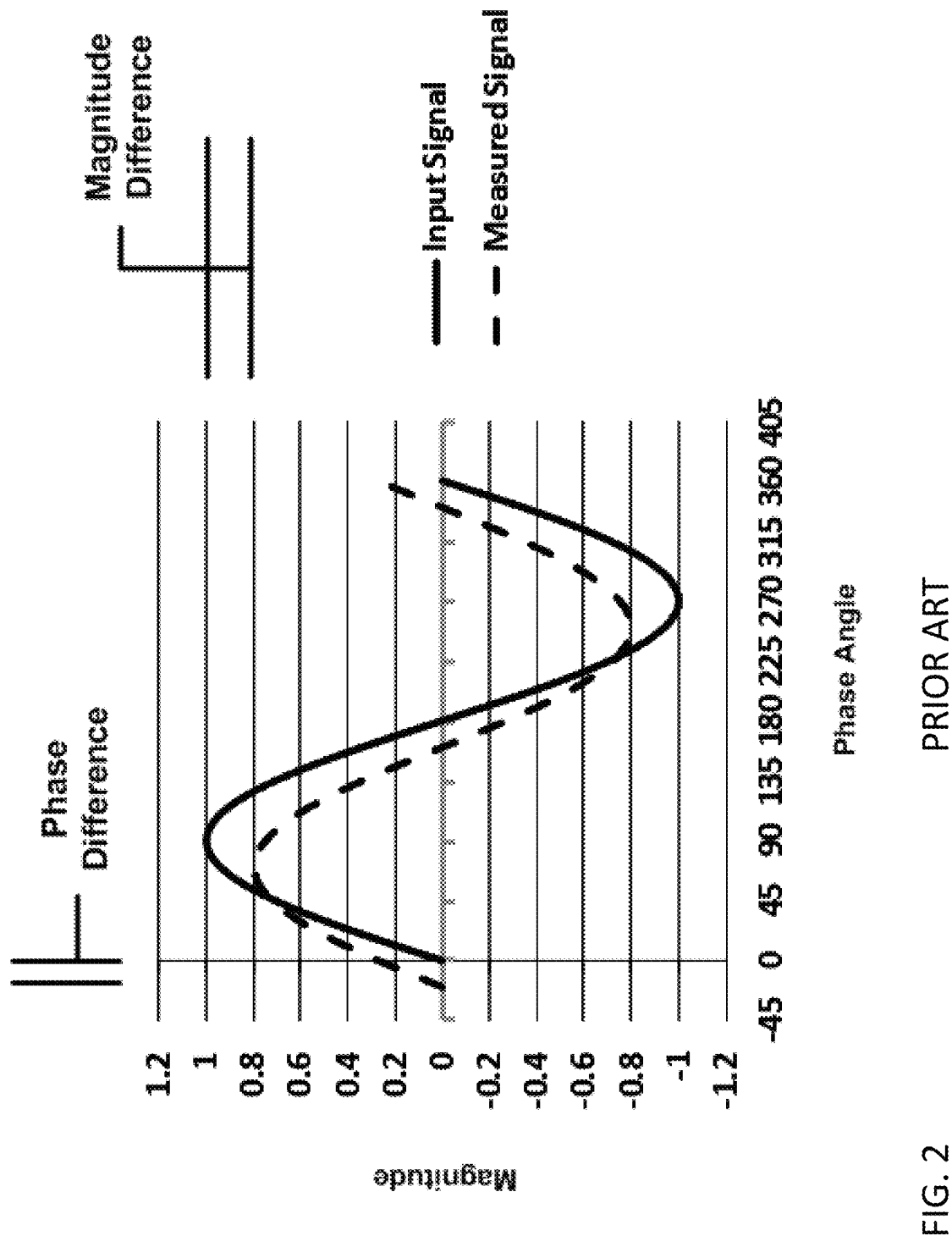
FIG. 2 is a graphical illustration of signals obtained during an impedance measurement.

As described in US Patent Publications 2013/0307564 and 2015/0137831 and U.S. Provisional Patent Applications No. 61/703,488, 61/932,400, and 62/103,835, a schematic depiction of a two-terminal measuring system for use in EMIT and EMIS is shown in FIG. 1. This schematic depiction shows an impedance sensor system where an electromagnetic signal, either current or voltage, is generated by a Direct Digital Synthesis Modulator (DDS) which is then transmitted through the MUT and to a comparator. The signal that is transmitted through the MUT is measured and transmitted to the comparator. As the signal is transmitted through the MUT, it is affected and modified by the effective dielectric (capacitance) and (resistivity) resistance of the MUT. This is shown in the schematic-graphical depiction in FIG. 2, where there is a change in the magnitude of the measured signal from the input signal, m, and a shift in the phase, φ. The comparator measures and records these changes, which are then used to compute the impedance characteristics of the MUT as discussed below.

In the discussion of the measurements and interpreting aspects of the complex impedance, it may be beneficial to define terms that may be calculated from the output of an electromagnetic measurement device which are the magnitude of the power difference between the transmitted signal and the signal that is transmitted through the MUT, m, and the phase angle, φ, shift between the transmitted signal and the signal transmitted through the MUT. These relations apply to both two-terminal and four-terminal measurements. Impedance (Z) is represented mathematically as a complex relation consisting of a real part, resistance, and an imaginary part, reactance:

$$Z=R+iX;$$

Z=the complex value of Impedance;
R=m*cos φ; the Resistance;
X=m*sin φ; the Reactance;

Resistance, R, is a material's opposition to the flow of electric current;

Reactance, X, is a material's opposition to alternating current due to capacitance (capacitive reactance) and/or inductance (inductive reactance);

Admittance, Y, is a complex quantity which is the inverse of impedance, and results in the definition of the terms of conductance and susceptance:

$$Y=1/Z=G+iB;$$

Susceptance, B, is a complementary representation of the reactance in the term admittance and is defined mathematically as:

$$B=-X/(R^2+X^2);$$

The Susceptance may be computed from the measured properties as follows:

$$B=\text{the Susceptance}=-\sin \varphi/m;$$

The Conductance, G, may be computed from the measured properties as follows:

$$G=\text{the Conductance}=\cos \varphi/m.$$

In the description of the various embodiments, the value of the impedance, Z, will be used in the various equations and relations pertaining to the measurements made of the voxels in the MUT and the computation of the sub-voxels. However, a value of the resistance, reactance, admittance, conductance, or susceptance may replace impedance in any of the examples below.

It should be noted that for a tomographic solution, only data at one frequency is required. However, for the use of a spectrographic analysis to characterize a property of the MUT, computations over a range of frequencies are required. That is, the above equations are applied to data from each frequency to obtain the impedance data over the range of frequencies. These data are then utilized by the Volume Differentiation and Removal (VDR) methodology as described in US Patent Publications 2012/0130212 and 2015/01337831 (each incorporated by reference in its entirety) and below for the specific geometry of a four-terminal measurement.

Figure 3:
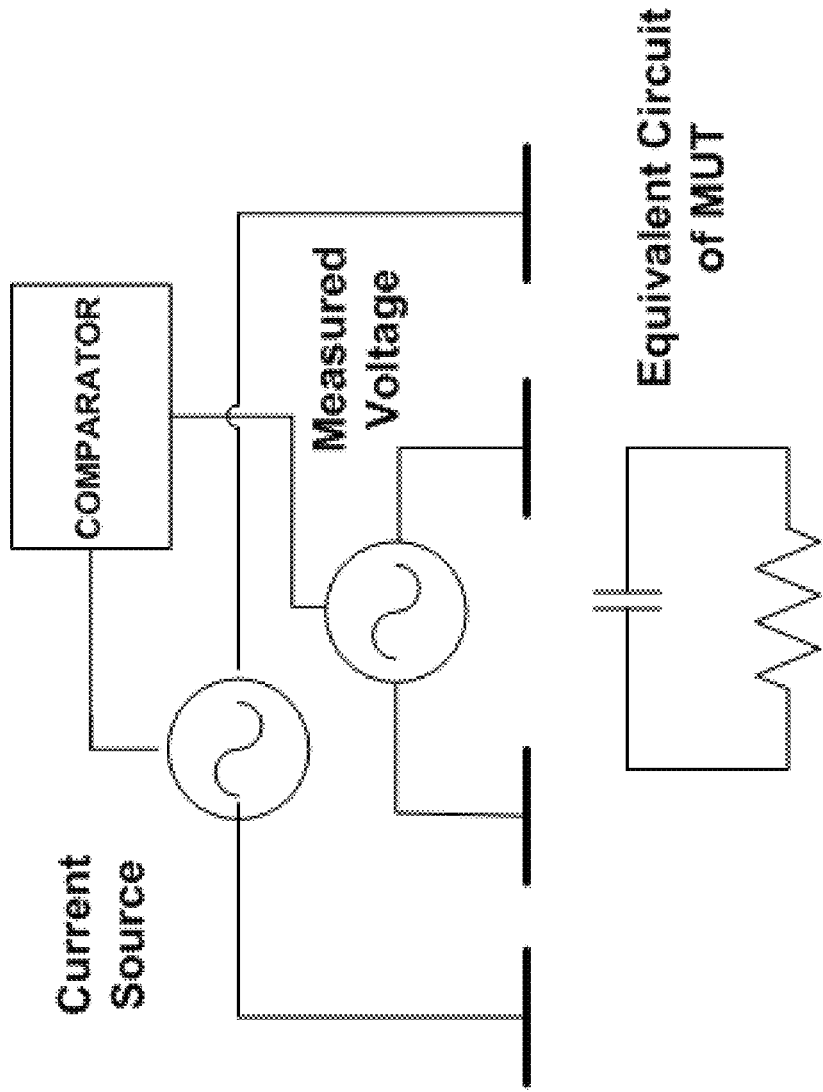
FIG. 3 is an illustration of a four-terminal measurement system according to the prior art.
Figure 4:
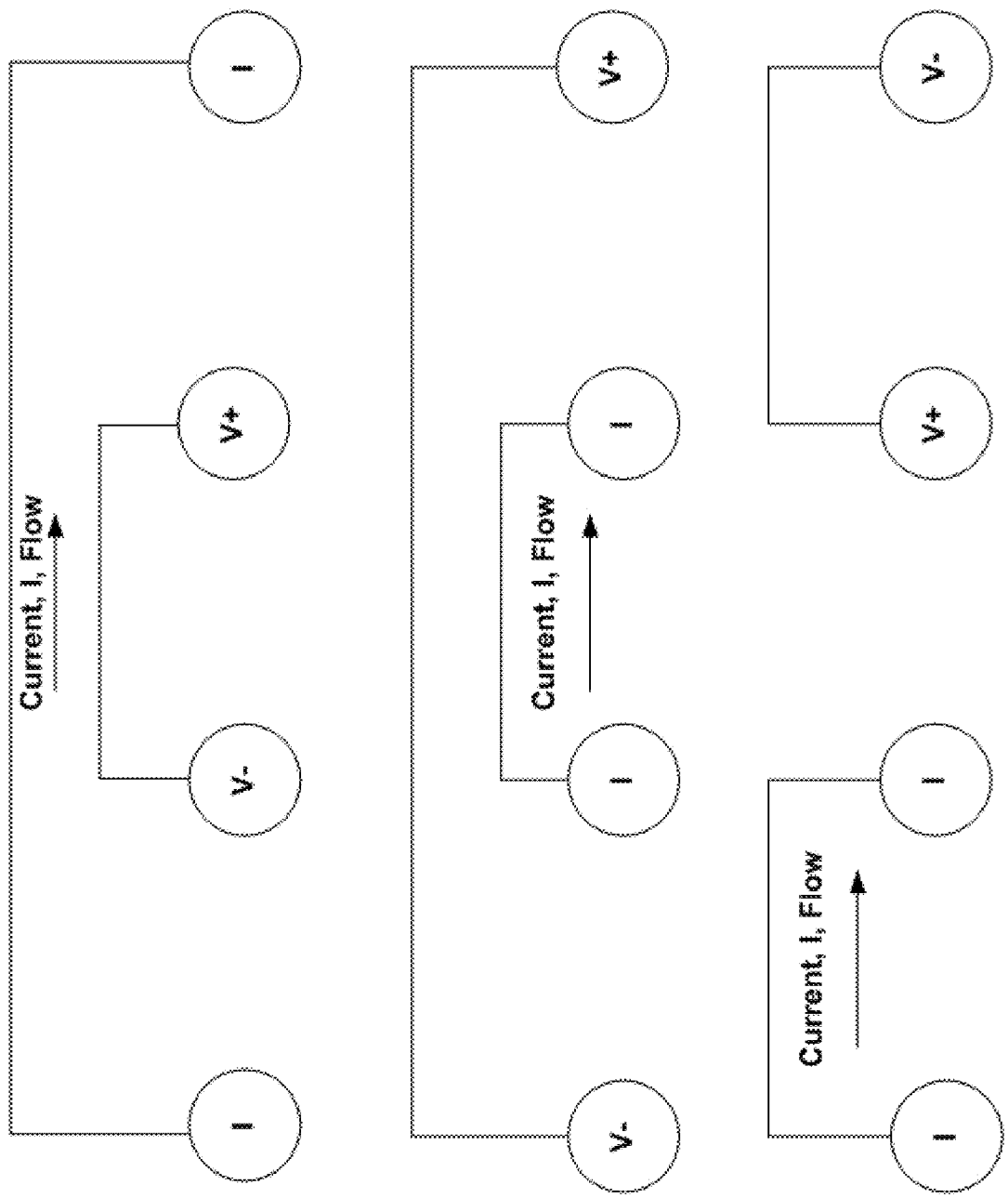
FIG. 4 is an illustration of four-terminal measurement electrode configurations.
Figure 5:
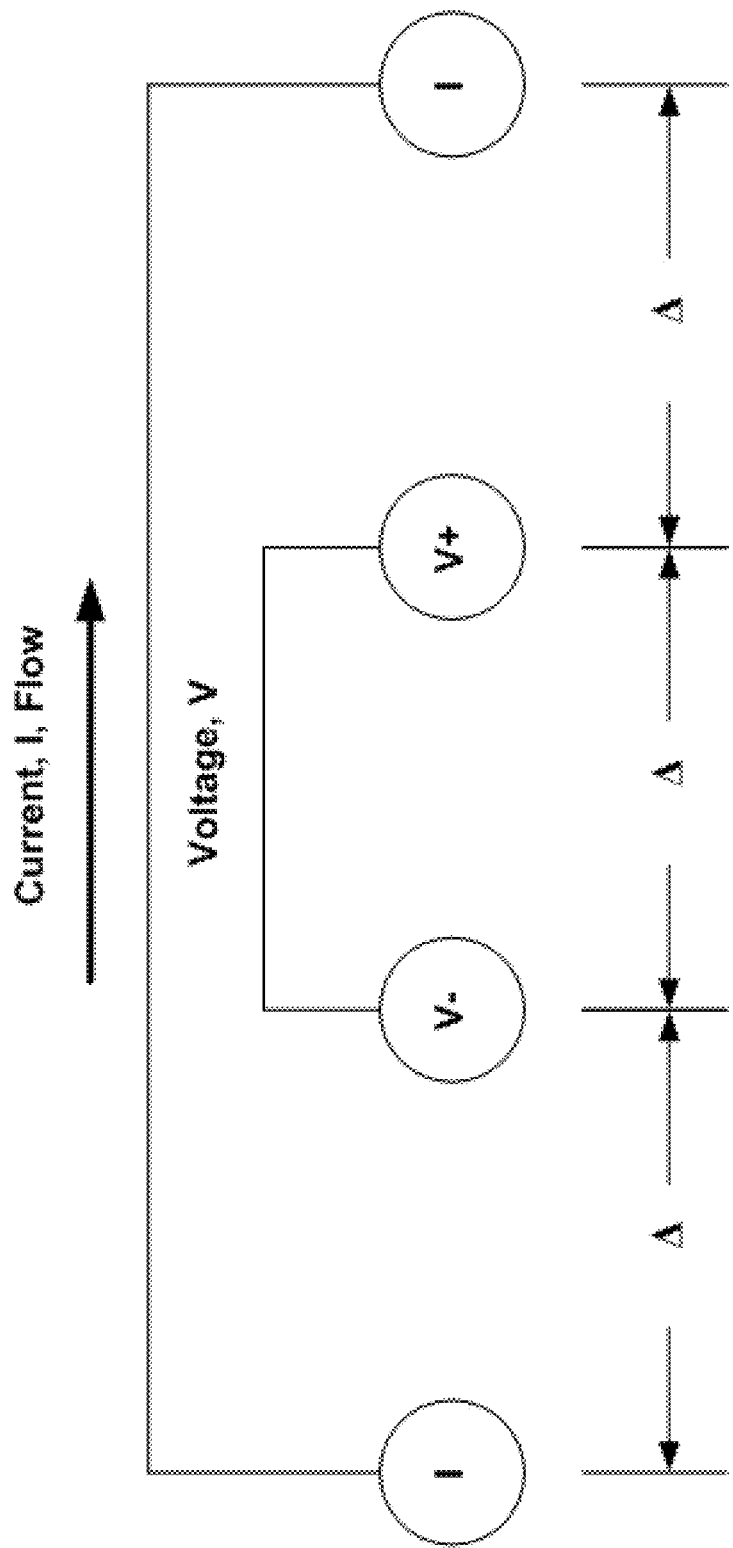
FIG. 5 is an illustration of a Wenner Array four-terminal measurement electrode configuration.

The four-terminal measurement described in US Patent Publication 2012/0130212 is illustrated in FIG. 3. The four terminals consist of two electrodes that transmit a current signal through the MUT and two electrodes that measure the resultant induced voltage across the MUT. Again, the input signal is affected by the dielectric and the resistivity properties of the MUT as discussed above and illustrated in FIG. 2. The configuration that is illustrated in FIG. 3 has the current terminals (electrodes) outside of the voltage terminals (electrodes). There are other possible configurations of the four-terminal measurement as illustrated in FIG. 4. The configuration shown in FIG. 4 includes current transmitting/receiving electrodes located outside of the voltage electrodes with identical spacing between electrodes. FIG. 5 shows a close-up view of this first configuration in FIG. 4. This configuration is known as a Wenner array. The equal spacing of the electrodes is required for the operation of VDR as explained in US Patent Publication No. 2012/0130212.

Figure 6:
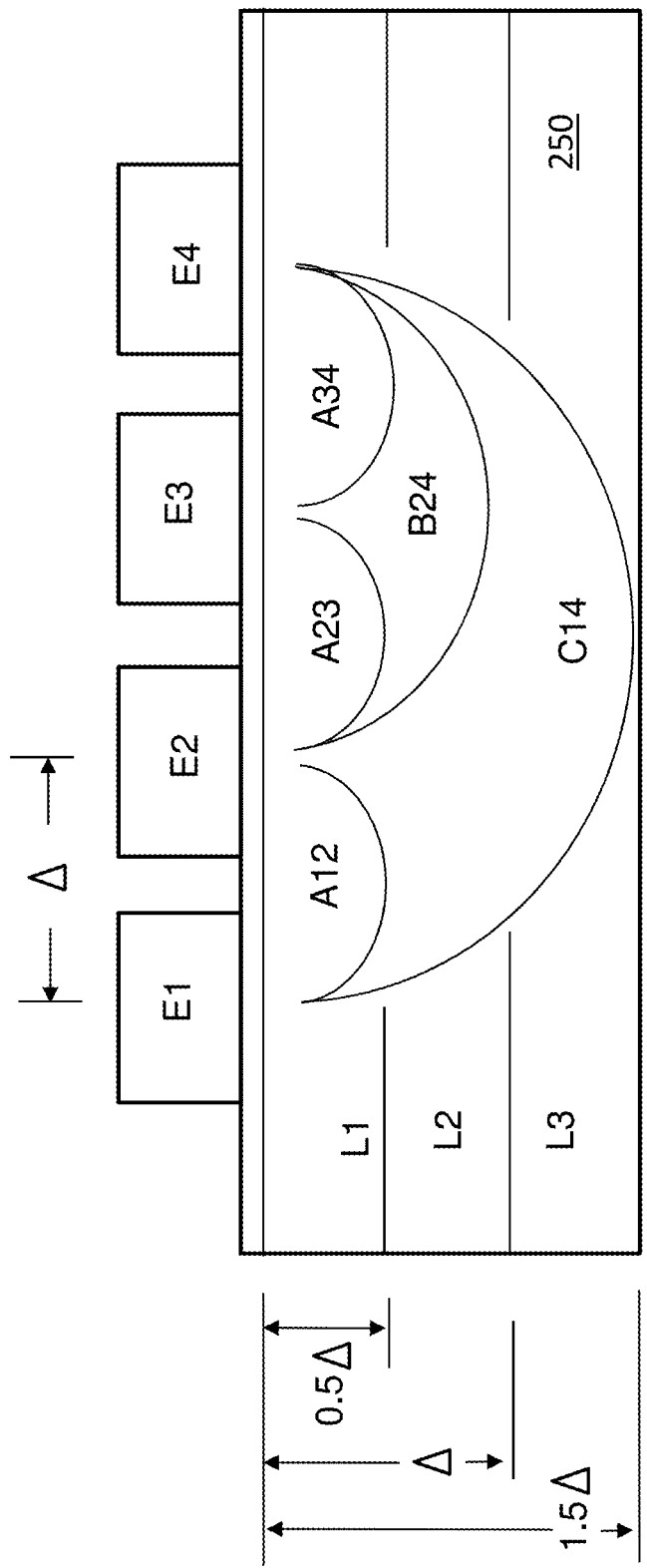
FIG. 6 is a schematic illustration of an electrode and material under test configuration.
Figure 7:
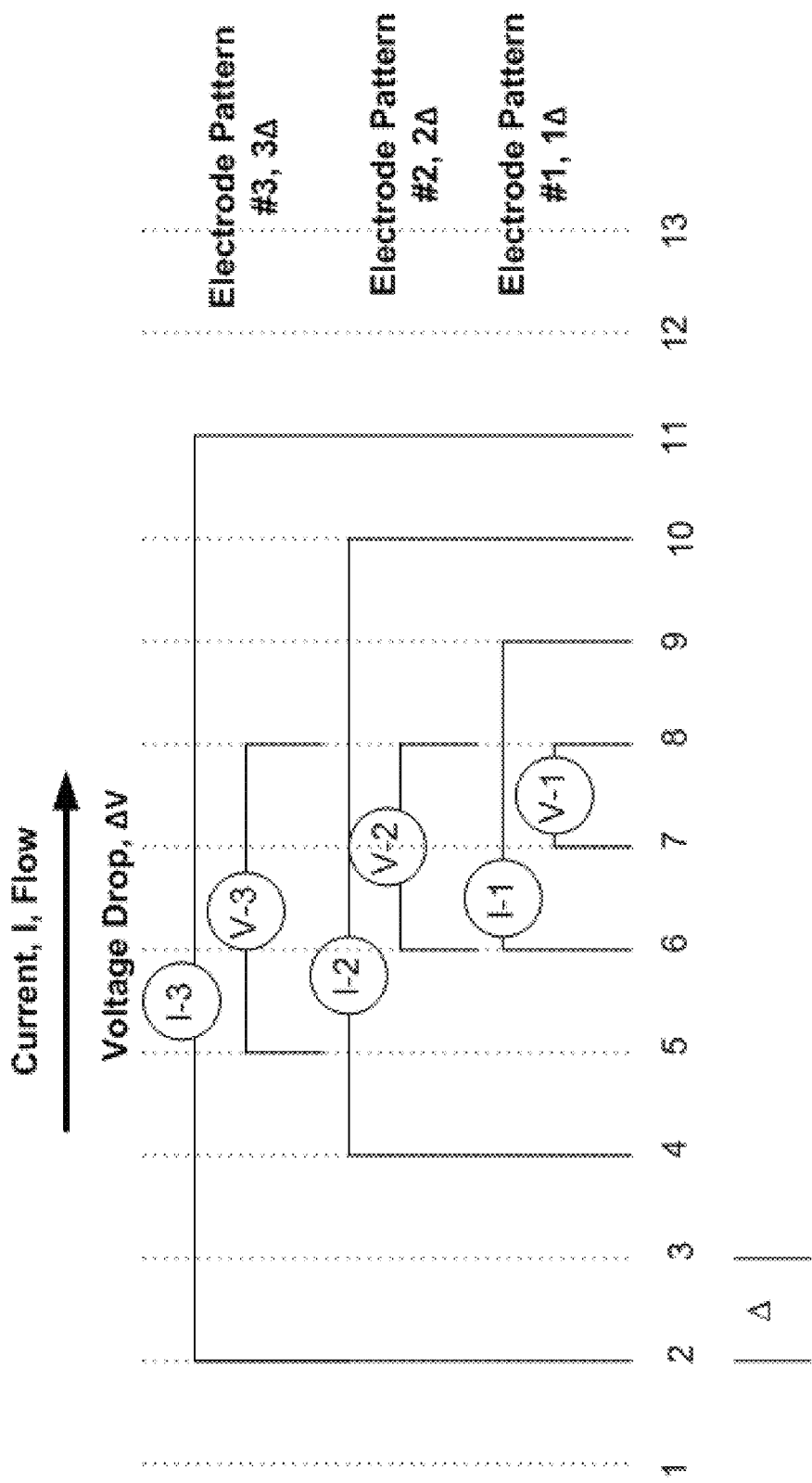
FIG. 7 is a schematic depiction of the electrode patterns according to embodiments of the disclosure.
Figure 8:
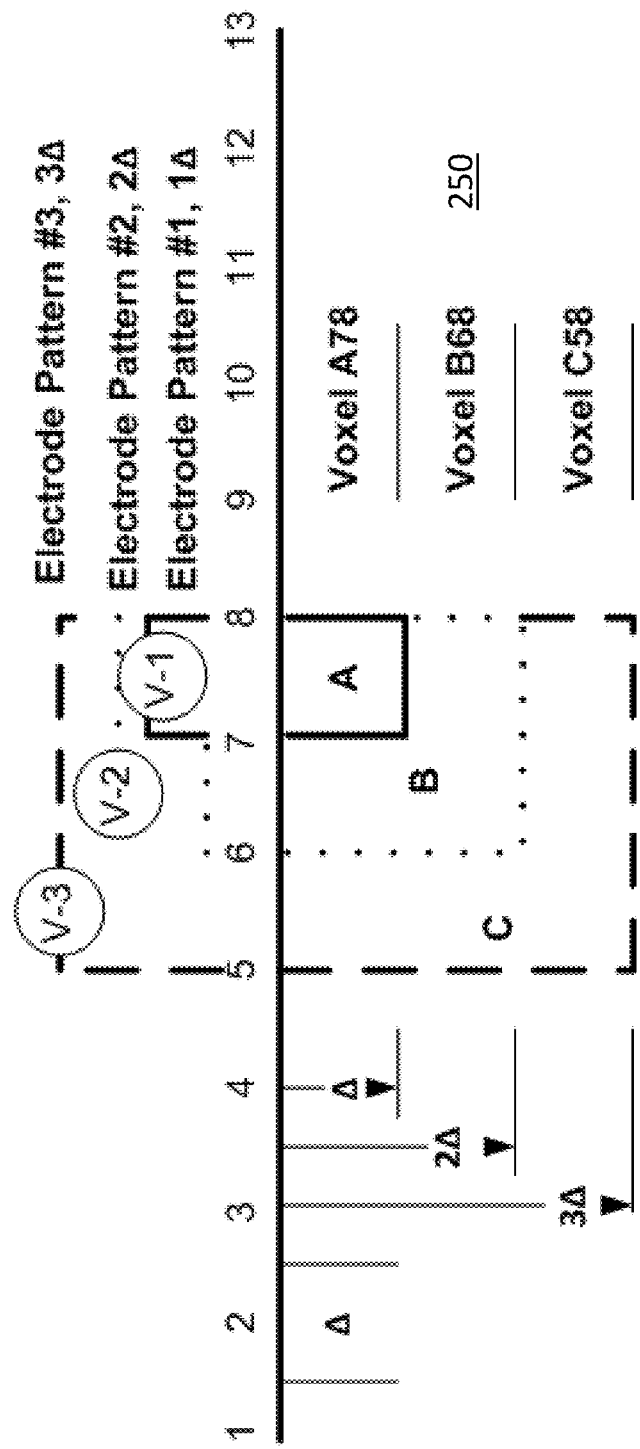
FIG. 8 is a schematic depiction of the voxels and sub-voxels with a three layer electrode pattern in a four-terminal measurement according to embodiments of the disclosure.
Figure 12:
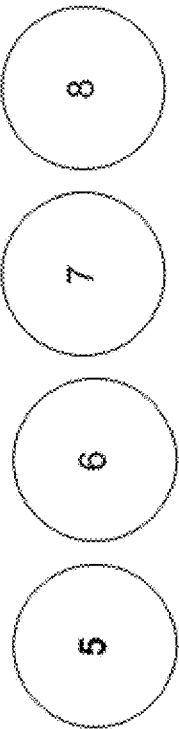
FIG. 12 shows a schematic depiction of the computation of sub-voxel impedance values using a four-terminal measurement according to embodiments of the disclosure.

In conventional systems, whether measurements are made by a two-terminal or four-terminal array, limitations still exist. One such limitation is that the sensing/measurement depth into the MUT is dependent on the physical spacing between the centers of the electrodes. FIG. 6 illustrates the two-terminal arrangement according to the conventional systems. This depiction illustrates three layers of MUT (L1, L2, L3), with a four-electrode sensor array (E1-E4). The notations of A12, B24 and C14 indicate that voxel A, B, or C are being measured between two electrodes. In these cases, a preference is not given to which electrode is the high or low side of the circuit. According to the conventional configuration, the depth being measured into the MUT is approximately one-half the distance between the centers of the probing electrodes (e.g., E1, E2, E3, E4). The spacing between electrode centers is shown as Δ in FIG. 6. In order to measure the impedance of the first layer L1, the electrode spacing is Δ (e.g. electrodes E1 and E2) and the layer depth is 0.5Δ. The impedance measurement of the second layer L2 requires the electrode spacing to be 2Δ (e.g. electrodes E1 and E3), where the second layer depth is Δ. For impedance measurement in the third layer L3, the electrode spacing is 3Δ (e.g., electrodes E1 and E4) and the layer depth is 1.5Δ. The penetration into the MUT 250 is different with a four-terminal measurement than with three or fewer terminals. In these cases, the depth being measured into the MUT 250 is approximately equal to the distance between two adjacent electrodes, assuming all four active electrodes are equally spaced. FIG. 7 illustrates three Wenner array electrode patterns on a linear array consisting of 13 electrodes. The spacing between electrode centers is Δ. The first Wenner electrode pattern (V-1) has an electrode spacing of Δ. The second Wenner electrode pattern (V-2) has an electrode spacing of 2Δ. The third Wenner electrode pattern (V-3) has an electrode spacing of 3Δ. Turning to FIG. 8, the arrangement of measured voxels (capital letters: A, B, and C) from the electrode configuration of FIG. 7, and their width and depth within MUT 250 are illustrated. FIG. 12 illustrates the computed sub-voxels (lower case letters: a, b, and c) and method of computing such sub-voxel values, with respect to FIGS. 7-8, and is discussed further herein. Returning to FIGS. 7-8, with continuing reference to FIG. 12, the voxels and sub-voxels are labeled as Axy and axy, respectively, where x and y are the electrodes in the corresponding pattern measuring those voxels. It should be noted that the rectangular shape of the voxels and sub-voxels in the figures is for illustrative purposes only, and that voxels and sub-voxels may take any number of shapes. A method to correct for the deviation from rectangular geometries is discussed below.

Figure 9:
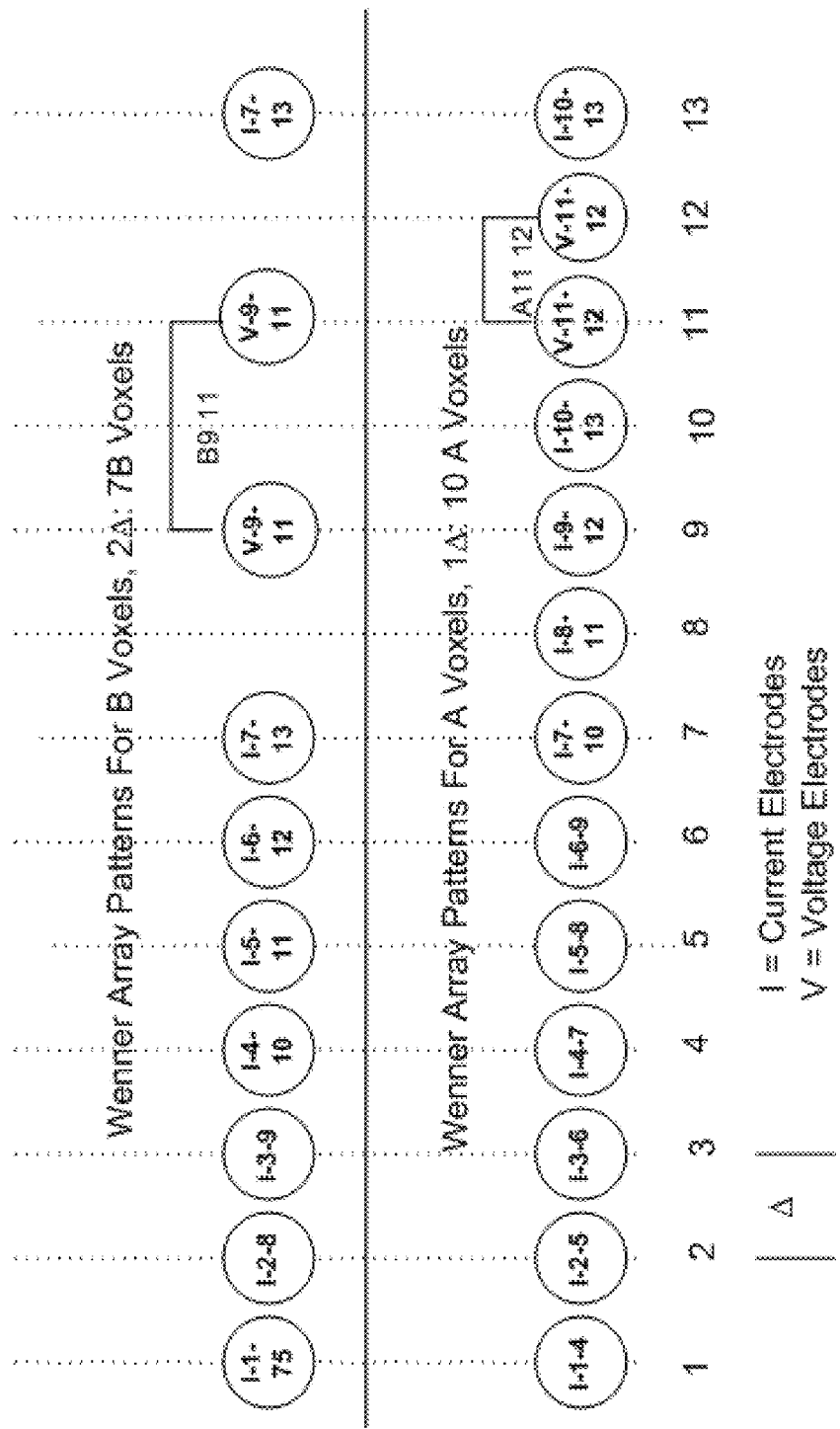
FIG. 9 shows a schematic depiction of electrode patterns for two three-layer measurements according to embodiments of the disclosure.
Figure 10:
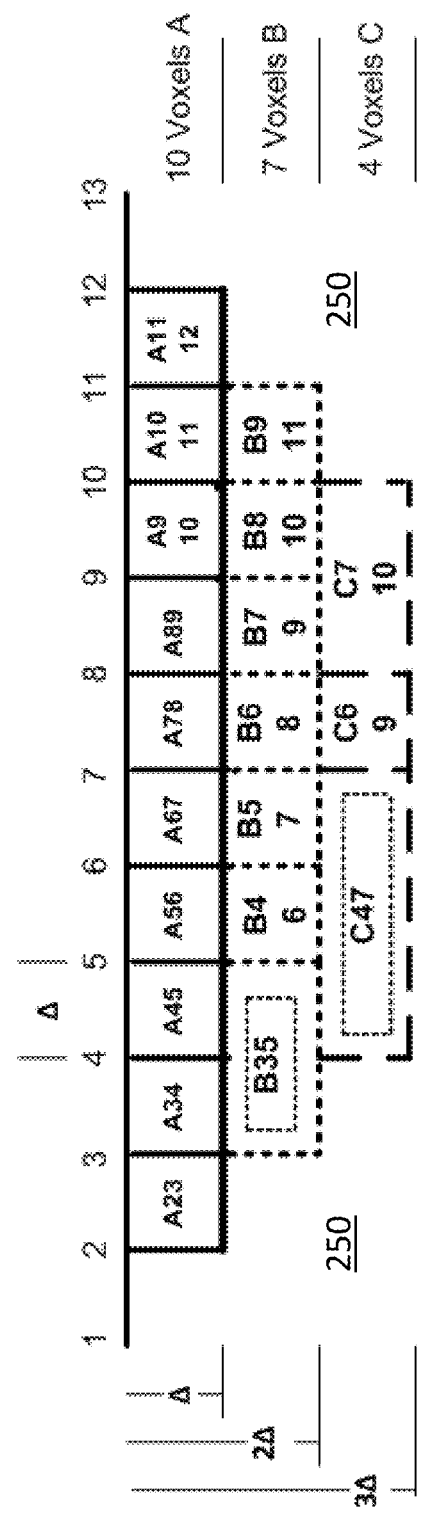
FIG. 10 shows a schematic depiction of measured voxels with an electrode pattern according to embodiments of the disclosure.

With a conventional two-terminal measurement, adequate data for the application of the VDR method may be obtained by securing readings between pairs of electrodes as shown in FIG. 6. For the four-terminal measurement according to various embodiments herein, various electrode patterns, each of which is part of a Wenner array, are used. The sequence of Wenner electrode patterns shown in FIG. 7 can be repeated multiple times across the linear electrode array. FIG. 9 illustrates the use of two sequences of Wenner electrode patterns in a linear electrode array with 13 electrodes, used to measure three layers of an MUT. In FIG. 9, a first set of Wenner electrode patterns is shown, having a spacing of Δ between the current-voltage-voltage-current electrodes of the four-terminal measurement, to provide measurements of the A voxels. The Wenner electrode patterns in the first set have a depth penetration into the MUT of Δ, and can be repeated ten (10) times, providing ten measurements of the A-voxels. FIG. 10 illustrates these ten possible A-voxels. Returning to FIG. 9, a second set of Wenner electrode patterns is shown, having a 2Δ spacing between the current-voltage-voltage-current electrodes of the four-terminal measurement, to provide a measurement of the B voxels. The Wenner electrode patterns in the second set have a depth penetration into the MUT of 2Δ, can be repeated seven times providing seven measurements of the B-voxels (FIG. 10) for this configuration. Similarly, a set of Wenner electrode patterns with a 3Δ spacing between the current-voltage-voltage-current electrodes of the four-terminal measurement provides a measurement of the C voxels, and a depth penetration into the MUT of 3Δ, which can be repeated four (4) times to provide four (4) measurements of C-voxels (FIG. 10) for this configuration. Turning to FIG. 10, with continuing reference to FIG. 9, where Δ is equal to approximately 0.6 mm, the center-to-center length of the measurements of each C-voxel is approximately 1.8 mm, and the total length of all four C-voxels is approximately 3.6 mm. If the number of electrodes in the linear array is increased to 17, the number of C-voxel measurements is increased to 8 measurements from 4 measurements, or a total center-to-center length of approximately 6.0 mm. If a fourth layer is to be measured, only one D-voxel can be measured with a linear array having 13 electrodes while 5 D-voxels can be measured with a linear array of 17 electrodes. If Δ is equal to approximately 0.6 mm, the center-to-center length of the measurements of each D-voxel is approximately 2.4 mm and the total length of all five D-voxels is approximately 4.8 mm.

Figure 11:
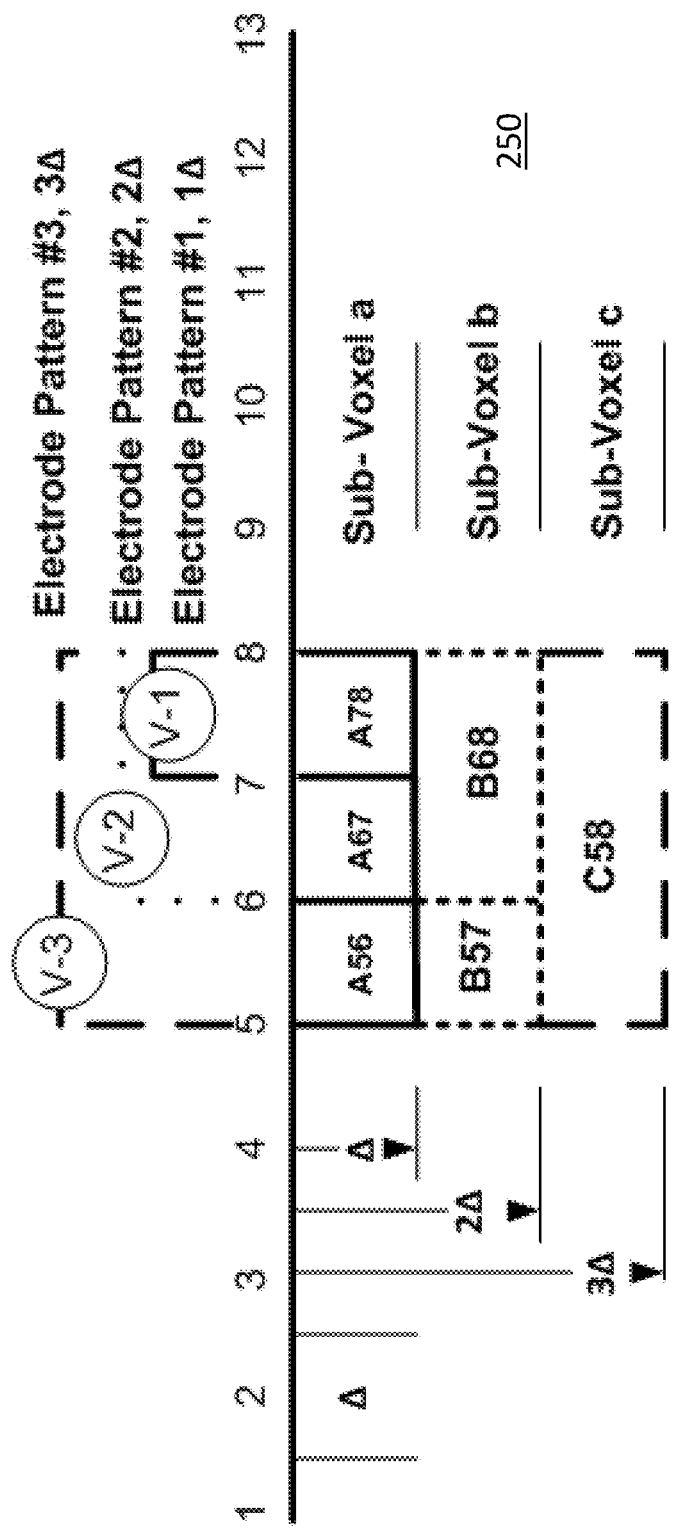
FIG. 11 shows a schematic depiction of the alignment of the measured voxels and computed sub-voxels according to embodiments of the disclosure.

One approach to VDR according to various embodiments of the disclosure is to collect multiple four-electrode data (about voxels), compute the values of sub-voxels from the voxel data, and combine the sub-voxels into voxel segments to compute other (non-computed) sub-voxels using the sub-voxel segments and the voxel data. This process is illustrated in the schematic diagrams in FIG. 11 and FIG. 12, which illustrate voxel layers A, B, and C, and sub-voxel layers a, b, and c, corresponding to four-terminal measurements on a linear electrode array (where electrodes of a larger linear electrode array are indicated by circular elements 5, 6, 7, and 8, respectively, in FIG. 12) such as those shown and described with reference to FIGS. 2, 8, 9, and 10. In various embodiments, a minimum of ten (10) data values (e.g., impedance values) are obtained (e.g., as described herein) in order to create a data set sufficient to calculate a standard deviation. In some cases, this process can include obtaining four-electrode data at several of distinct electrode configurations for a given MUT. However, in other cases, this process can include obtaining four-electrode data at one or two distinct electrode configurations, where each configuration yields five (5) or more data values. FIG. 11 shows an example including six data points (three voxel A measurement; two voxel B measurements; and one voxel C measurement). The measurements obtained in the configuration illustrated in FIG. 11 could be combined with another set of measurement data in order to build a data set sufficient to calculate a standard deviation. As shown at different depths within the MUT, sub-voxel a overlies sub-voxel b, which overlies sub-voxel c. According to particular embodiments, for a given surface area at the MUT, voxels (e.g., Axy, Bxy, Cxy) within a given sub-voxel layer (e.g., a) are assumed to have a substantially uniform density within that sub-voxel layer, despite the fact that each sub-voxel layer may have a distinct number of voxels (e.g., three in sub-voxel a; two in sub-voxel b, one in sub-voxel c). The computed impedance values of sub-voxels axy are identical to the measured voxels Axy. This layer of measured voxels and computed sub-voxels is assumed to be uniform. The primary determination of the uniformity of the first layer of voxels is the size of the voxel relative to the property changes expected in that layer of the MUT examined over the range of the larger voxels for which the sub-voxel properties are to be computed. For example, in the case of a glucose monitor, the first layer is the epidermis. There are minimal changes expected in the epidermis over the range of the largest voxel to be measured, which are the C or D layers. In this example, for the C layer, the length of the measured volume is 9Δ, and for the D layer, it is 12Δ. Because for this application Δ is in the order of approximately 0.6 mm, the maximum expanse of the measurement for the D layer would cover approximately 7.2 mm (0.28 in). The uniformity of the second, third, fourth and subsequent sub-voxel layers are determined by the statistical deviation process noted above. While impedance variation is not expected to be significant within a given voxel layer (x direction), impedance variation between voxel layers (z direction) is expected. That is, based upon the measured impedance of a voxel, and given the calculated standard deviation of values within a layer, the density of a given voxel/sub-voxel can be calculated according to various embodiments. For example, as described herein, physical properties or characteristics (e.g., densities) of particular layers of a MUT can be calculated based upon the measured impedance values of those layers. In some cases, the characteristics (e.g., densities) of a material, along with corresponding impedance responses of that material, are known ahead of time (e.g., physically or otherwise measured in a controlled setting), and can be stored in a database, table, etc. for reference. As noted herein, according to various embodiments of the disclosure, the statistical impedance variation within a given layer of an MUT 250 can be calculated using a series of measurements (e.g., ten or more) sufficient to form a reliable data set. This statistical impedance variation data can be used to determine which subsequent impedance measurements are valid (e.g., within one standard deviation of the mean). As further noted herein, within a given MUT layer (e.g., the epidermis layer of human tissue), the impedance response within a sub-voxel layer can be assumed to be approximately uniform (e.g., voxels A56, A67, A78), and the overall impedance response of a given sub-voxel layer within an MUT layer (e.g., sub-voxel axy) can be assumed to be approximately equivalent to the overall impedance response of a distinct sub-voxel layer (e.g., sub-voxel bxy). Based upon this principle, and given that each sub-voxel layer measured may have a distinct number and orientation of voxels when compared with overlying or underlying sub-voxel layers, various approaches allow for calculating the impedance of voxels within a given MUT layer based upon measurement(s) of other voxels within that MUT layer.

Figure 13:
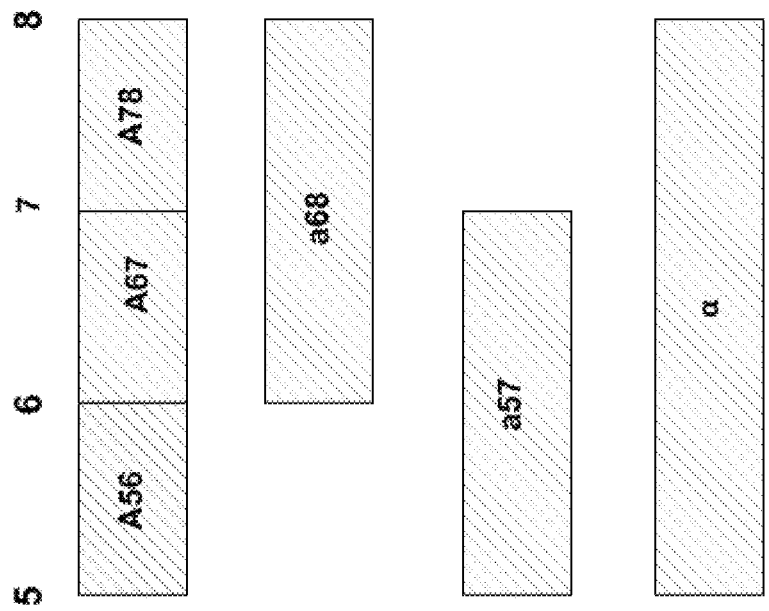
FIG. 13 shows a schematic depiction of the computation of an impedance of a sub-voxel using a four-terminal measurement according to embodiments of the disclosure.
Figure 14:
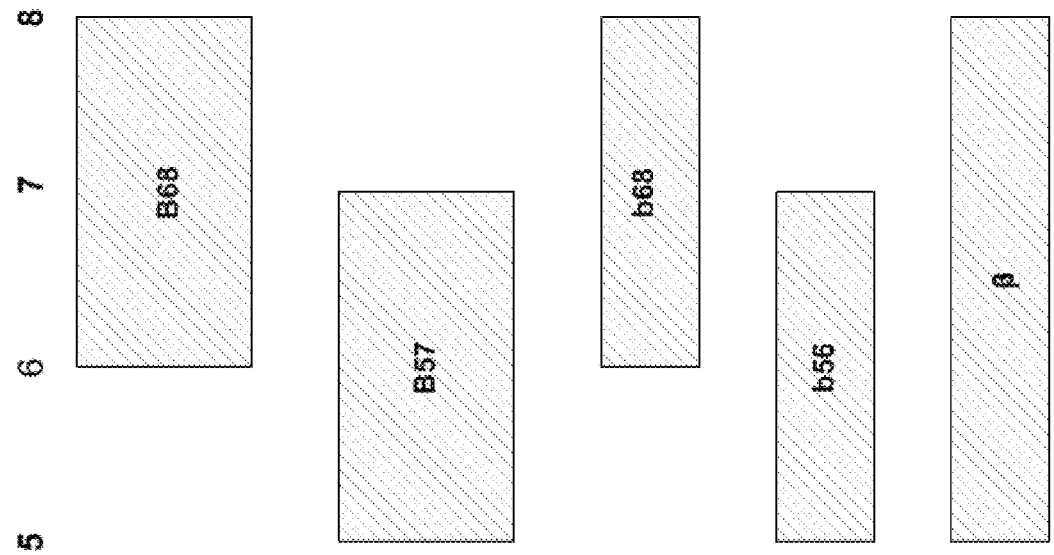
FIG. 14 shows a schematic depiction of the computation of an impedance of sub-voxels using a four-terminal measurement according to embodiments of the disclosure.

Computed non-uniformities in a sub-voxel in any layer are included in the computational methodology for subsequent layers. Computed non-uniformities in subsequent layers are used in the thresholding process (e.g., factored into a thresholding algorithm) described herein. Referring to the examples illustrated in FIGS. 13-15, sub-voxel a57 (FIG. 13) is the series combination of voxels A56 and A67. Sub-voxel a68 (FIG. 13) is the series combination of voxels A67 and A78. The sub-voxels are serially combined to form sub-voxel segment a (FIG. 13). In FIG. 14, sub-voxel β is the series combination of sub-voxels b57 and b68. According to various embodiments, sub-voxel segments α and β are combined in a parallel fashion with sub-voxel c58 to represent voxel C58 (shown in spatial depiction of FIG. 15). The mathematical process used to calculate the sub-voxel values is illustrated in the equations and corresponding schematic depictions of the voxel/sub-voxel combinations shown in spatial depictions of FIGS. 13, 14, and 15.

Figure 15:
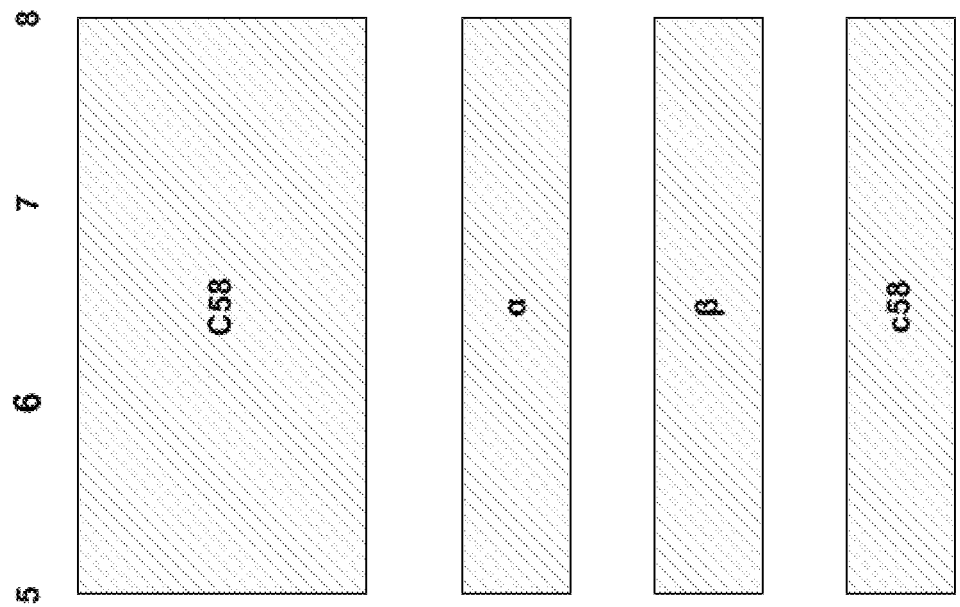
FIG. 15 shows a schematic depiction of the computation of an impedance of a sub-voxel using a four-terminal measurement according to embodiments of the disclosure.

The general form of the equations depicted in FIGS. 13-15 according to various embodiments is presented as follows:

$$Z_{a(n,n+1)} = Z_{A(n,n+1)}$$

$$Z_{b(n,n+2)} = \frac{(Z_{A(n,n+1)} + Z_{A(n+1,n+2)}) * Z_{B(n,n+2)}}{(Z_{A(n,n+1)} + Z_{A(n+1,n+2)}) - Z_{B(n,n+2)}}$$

$$Z_{b(n+1,n+3)} = \frac{(Z_{A(n+1,n+2)} + Z_{A(n+2,n+3)}) * Z_{B(n+1,n+3)}}{(Z_{A(n+1,n+2)} + Z_{A(n+2,n+3)}) - Z_{B(n+1,n+3)}}$$

$$Z_{a(n,n+3)} = Z_{A(n,n+1)} + Z_{A(n+1,n+2)} + Z_{A(n+2,n+3)}$$

$$Z_{\beta(n,n+3)} = \delta Z_{b(n,n+2)} + (1-\delta) * Z_{b(n+1,n+3)}$$

$$Z_{c(n,n+3)} = \frac{Z_{a(n,n+3)} * Z_{\beta(n,n+3)} * Z_C(n,n+3)}{(Z_{a(n,n+3)} * Z_{\beta(n,n+3)}) - (Z_{a(n,n+3)} + Z_{\beta(n,n+3)}) * Z_{C(n,n+3)}}$$

According to various embodiments, the above equations may be modified based upon the geometry of the electrode arrangement to account for the differences between the measured volume of the MUT 250 and the assumed shape of the voxels and sub-voxels in that volume. To account for relative changes in the geometry of electrode arrangements, a geometry factor may be determined and applied to the measured impedance of the voxels as follows:

$$Z_{A(n,n+1)}$$

$$\gamma_b Z_{b(n,n+2)} = \gamma_b \left( \frac{(Z_{A(n,n+1)} + Z_{A(n+1,n+2)}) * Z_{B(n,n+2)}}{(Z_{A(n,n+1)} + Z_{A(n+1,n+2)}) - Z_{B(n,n+2)}} \right)$$

$$\gamma_b Z_{b(n+1,n+3)} = \frac{(Z_{A(n+1,n+2)} + Z_{A(n+2,n+3)}) * Z_{B(n+1,n+3)}}{(Z_{A(n+1,n+2)} + Z_{A(n+2,n+3)}) - Z_{B(n+1,n+3)}}$$

$$\gamma_a Z_{a(n,n+3)} = \gamma_a (Z_{A(n,n+1)} + Z_{A(n+1,n+2)} + Z_{A(n+2,n+3)})$$

$$\gamma_\beta Z_{\beta(n,n+3)} = \gamma_\beta (\delta Z_{b(n,n+2)} + (1-\delta) * Z_{b(n+1,n+3)})$$

$$\gamma_c Z_{c(n,n+3)} =$$

$$\gamma_c \left( \frac{Z_{a(n,n+3)} * Z_{\beta(n,n+3)} * Z_C(n,n+3)}{(Z_{a(n,n+3)} * Z_{\beta(n,n+3)}) - (Z_{a(n,n+3)} + Z_{\beta(n,n+3)}) * Z_{C(n,n+3)}} \right)$$

where: A, B, and C are the measured voxel volumes;
a, b, and c are the computed sub-voxel properties;
n is the electrode array number;
δ is the contribution of $Z_{b(n,n+2)}$ relative to $Z_{b(n+1,n+3)}$ for the computation of $Z_\beta$, and $\gamma_x$ is a geometry factor for the xth voxel. The geometry factor is a correction applied to the planar electrodes to correlate the values read with a parallel plate electrode ε. The parallel plate equation is:

$$C = \frac{A}{d}\varepsilon;$$

where:
C is the capacitance;
ε is the dielectric; and
A/d is equivalent to the geometry factor, γ.

Various approaches of the disclosure allow for determining a physical property of a sub-voxel or a number of sub-voxels of the MUT 250. In various embodiments, a number of measurements of the physical property (or properties) or characteristic (e.g., glucose level, lactose level, density, metabolite level, etc.) of interest are measured by conventional means and correlated with the measured and computed complex electromagnetic spectrographic impedance (of the voxels and sub-voxels) using the arrays/systems/approaches described herein. In various embodiments, the number of measurements can be sufficiently large such that the resulting correlation is statistically significant. The impedance measurements can be made with the same type of array that will be used to inspect unknown MUTs, or in other embodiments, a parallel plate electrode arrangement may be used. Regardless of the array geometry, the measurements may also be made over a range of frequencies. Further embodiments include a method of developing an algorithm to correlate selected electromagnetic spectrographic impedance characteristics of the voxels or sub-voxels over the selected frequency range to the desired physical properties of the MUT 250, which may use any number of well-known correlation methods, such as, analysis of variations (ANOVA), neural networks, and multiple regressions. A determination as to which process, impedance characteristic(s) and frequency range may ensure that the best fit may be made by selection of the ones that provide the most statistically significant results to the independently determined desired physical properties of the MUT 250. The selection of the process that provides the statistically significant correlation algorithm is then applied with the identified impedance characteristics over the selected frequency (or frequencies) to determine the desired physical properties of the MUT 250. That is, as noted herein, a pre-derived model or data set is used to form the basis of an expected impedance response for the MUT 250. This model or data set can be formed by empirical testing, or may be obtained from one or more data sources known in the art (e.g., previous studies, data compilations, etc.). According to various embodiments, measurements of the MUT 250 are made (as described herein with respect to obtaining impedance data from one or more electrode configurations), and those measurements are compared with the pre-derived model or data set to determine how those measurements compare with the standard deviation from that pre-derived model or data set. Impedance measurements (and associated frequencies) used to make voxel characteristic determinations are selected based upon their adherence to the standard deviation, e.g., those with the smallest standard deviation (e.g., within one standard deviation, or within X*standard deviation) are selected for use in calculating other voxel values not measured. In some cases, impedance measurements are taken in several sets (of statistically significant data), and then those several sets are compared with the standard deviation from the pre-derived model or data set. In this embodiment, only the data set that is closest to the standard deviation is used to determine voxel values and calculate corresponding characteristics of one or more voxels.

Figure 16:
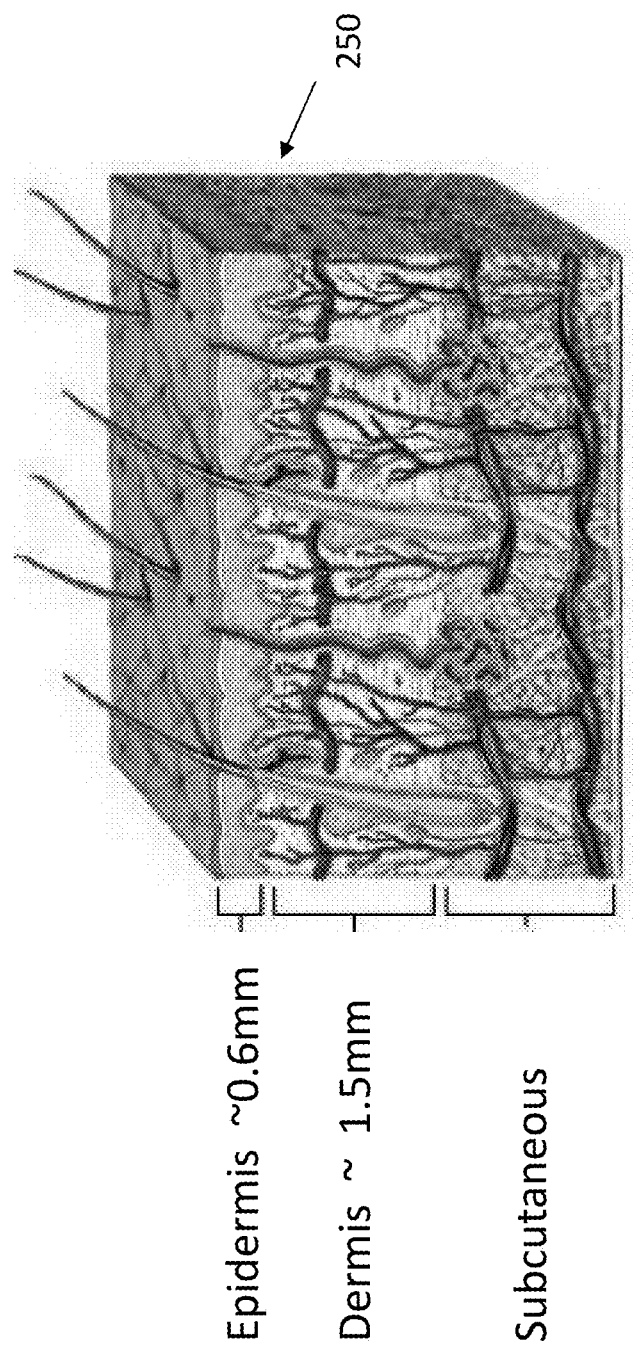
FIG. 16 is an illustration of human skin and the thickness of the epidermis and the dermis as an example of a material under test.

One example of an MUT 250 is shown in the schematic depiction of FIG. 16, which illustrates human skin. A first reason to apply VDR to human skin is to first locate a blood rich area with tomography by securing repeated readings using the Wenner configuration of electrode patterns across the linear array of electrodes at a single frequency as described herein. Following this initial application, VDR may be applied to the data collected with only the segment of the linear electrode array that includes the blood-rich volume over a range of frequencies by applying a threshold criterion. In the case of skin, blood has an impedance value about ten times that of fat and skin tissue cellular structure, excluding the blood in the capillaries. A volume of skin with more blood will have an impedance value higher than one with less blood. Since the VDR methodology is able to isolate the impedance characteristics of the sub voxels of subsurface layers, anomalous values of impedance may be related to specific sub-voxels. Sub-voxels with more blood in them will have a higher computed impedance. In simple form, the sub-voxel in any layer with the maximum impedance value may be assumed to have the highest concentration of blood within that sub-voxel. Using this basic approach, the sub-voxel with the highest computed value of impedance may be selected and used as the focus for an electromagnetic impedance spectrographic examination to relate to the desired physical property of the MUT. Using only the sub-voxel that is identified as containing the blood-rich volume, the calculated electromagnetic impedance spectroscopy is correlated with the desired characteristic property according to the correlation methodology described herein, e.g., the value of a metabolite such as glucose. By excluding the surface measurements and applying only the calculated sub-voxel impedance characteristics, the confounding factors of the surface measurement (e.g., the epidermis) can be removed for consideration in the spectrographic correlation.

According to embodiments, there are various additional approaches to selecting the desired sub-voxel to examine using electromagnetic impedance spectroscopy other than the simplistic approach described above. In one approach, all of the computed impedance characteristics of all of the sub-voxels, excluding the first or A layer, can be combined to determine the standard deviation of all the readings. The sub-voxel which has the largest standard deviation greater than the mean could be selected as the target sub-voxel. Again, using the standard deviation calculation of all the computed impedances of all of the sub-voxels, a test can include selecting any sub-voxel with a standard deviation that exceeds a specified value greater than the mean. Depending on the MUT and the target property, a sub-voxel measurement that differs from the mean by one standard deviation may be considered as significant. In other cases, depending on the MUT and the target property a sub-voxel measurement may need to differ from the mean by two or three standard deviations. A threshold of a sub-voxel measurement that differs from the mean by three times the standard deviations is a high-threshold test that the deviation from the mean is statistically significant. That is, according to various embodiments, impedance measurements deviating from the mean impedance level by one or more standard deviations can indicate readings capturing blood-rich areas.

In the above human-skin example, for most locations on the body where a measurement would be taken, the epidermis (A-voxel and a-sub-voxel) has a thickness of approximately 0.6 mm. On the eyelids, the epidermis is approximately 0.05 mm thick, and on the palms of the hands and the soles of the feet, the epidermis is approximately 1.5 mm thick. In one preferred measurement location (the deltoid area and the abdomen), the dermis is approximately 1.5 mm thick. As such, in this example, the A-voxel measurement would be almost exclusively focused on the epidermis layer (A-voxel depth of approximately $\Delta=0.6$ mm); the B and C-voxels (B-voxel depth of $2\Delta=1.2$ mm, and C-voxel of depth $3\Delta=1.8$ mm) would include the epidermis and dermis layers; and the D-voxel (depth of $4\Delta=2.4$ mm) would include the epidermis, dermis, and subcutaneous layers. It should be noted that the dermis layer contains the capillary bed of blood vessels which would constitute a blood rich volume, and the subcutaneous layer includes a layer of fat and connective tissue that contain larger blood vessels and nerves. It is known that while the epidermis and dermis layers at the same locations on the body tend to be of similar thicknesses for all individuals, there is considerable variation in the thickness of the subcutaneous layer.

Figure 17:
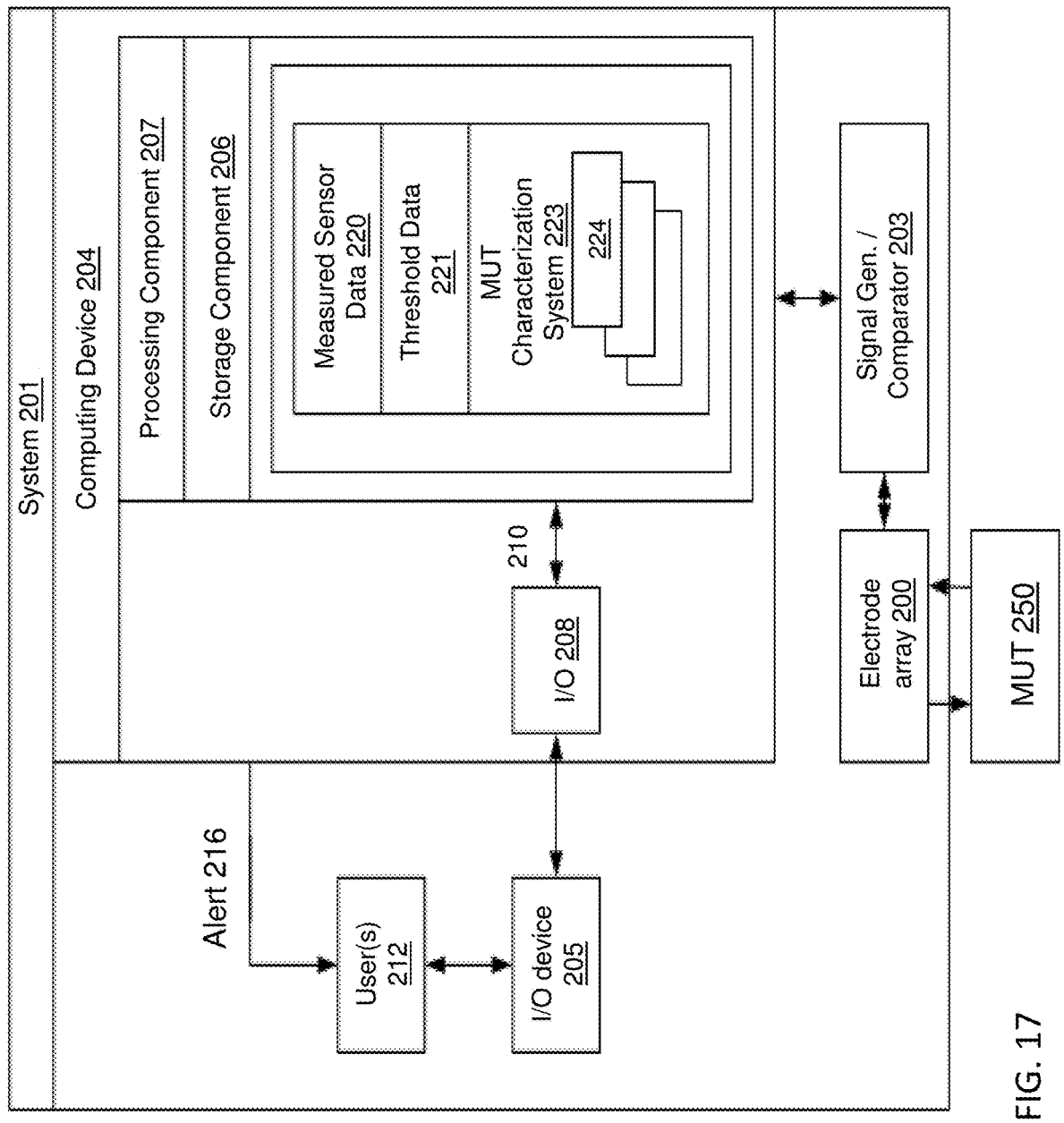
FIG. 17 shows a schematic depiction of an environment including a system according to various embodiments of the disclosure.
Figure 18:
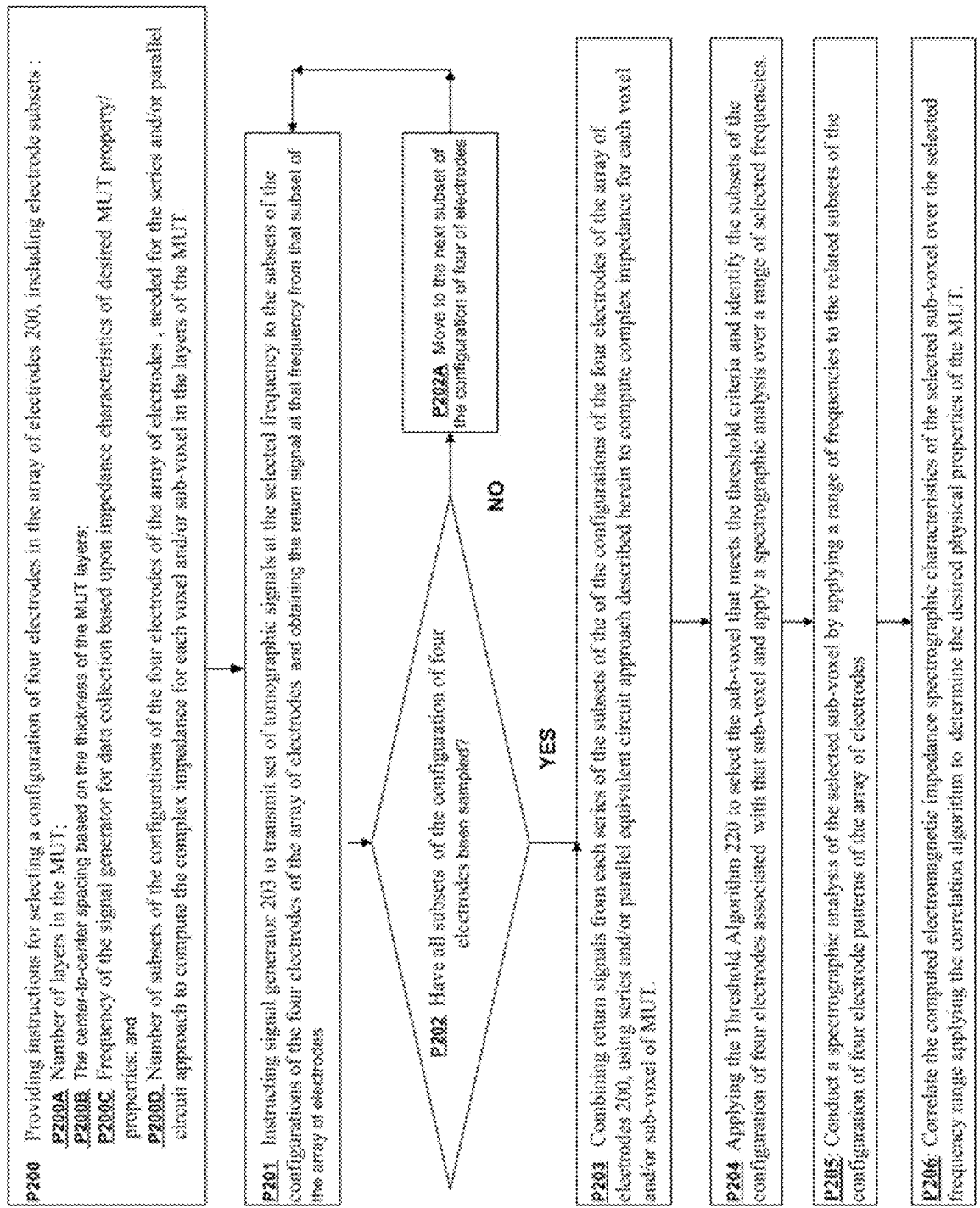
FIG. 18 shows a flow diagram illustrating a process according to various embodiments.

In some cases, as shown in FIG. 17, a sensor system 201 is described which includes an array of electrodes 200 for communicating (conductively or non-conductively) with a surface and a subsurface beneath the surface of an MUT 250. As described herein, the array of electrodes 200 can be configured in a plurality of distinct ways to detect, and potentially determine the characteristics of, an MUT 250. The sensor system 201 can further include a signal generator/comparator 203 which transmits the signal (e.g., operating at a single frequency or over a range of frequencies) through the MUT 250, receives and compares the return signal with the transmitted signal, and provides at least one computing device 204 with the measured data 220. The signal generator 203 is operably connected (e.g., hardwired) with the array of electrodes 200. The at least one computing device 204 is operably connected with the signal generator 203 (e.g., wirelessly and/or hard-wired) and the array of electrodes 200 (e.g. hard-wired or simply via common connection with the signal generator), and is configured to perform various functions described herein. Referring to FIG. 17, the at least one computing device 204 is configured to perform the method described below FIG. 18 shows a flow diagram depicting a method according to various embodiments of the disclosure which comprise a sequence of processes (not necessarily in the order presented). The method can be used to characterize select volumes of an MUT 250 using a series of four electrode patterns of the array of electrodes 200 by selecting pattern combinations of four electrodes in the array 200 as specifically illustrated in FIG. 9 and FIG. 10. As shown, the flow diagram can include processes including:

Process P200: Providing instructions for selecting a configuration of four electrode patterns in the array of electrodes 200, including electrode subsets, based upon at least one of: A) Number of layers in the MUT 250; B) Center-to-center spacing between electrodes 200 based upon the thickness of the desired layers of the MUT 250; C) Frequency of the signal generator 203 for data collection based upon impedance characteristics of desired MUT 250 property/properties; and/or D) Number of subsets of the configuration of the four electrode pattern of the array of electrodes 200, needed for the series and/or parallel circuit approach to compute the complex impedance for each voxel and/or sub-voxel in the layers of the MUT 250;

P201: Instructing signal generator 203 to transmit signals at the selected frequency to the subsets of the configurations of the four electrode pattern of the array of electrodes 200 and obtaining the return signal;

D202: Have all subsets of the configuration of four electrode pattern of the array of electrodes 200 been sampled?;

P202A: No to D201A, move to next subset of array of electrodes 200, loop back to P201;

P203: Combine return signals from each series of the subsets of the of the configurations of the four electrode patterns of the array of electrodes 200, using series and/or parallel equivalent circuit approach described herein to compute complex impedance for each voxel and/or sub-voxel of MUT 250;

P204: Apply the Threshold Selection algorithm 221 to select the sub-voxel that meets the threshold selection criteria (e.g., exceeds one or more standard deviations from mean impedance value), and identify the subsets of the configuration of four electrode pattern associated with that sub-voxel;

P205: Conduct a spectrographic analysis of the selected sub-voxel by applying a range of frequencies to the related subsets of the configuration of four electrode patterns of the array of electrodes 200; and P206: Correlate the computed electromagnetic impedance spectrographic characteristics of the selected sub-voxel over the selected frequency range by applying the correlation algorithm to determine the desired physical properties of the MUT 250.

Returning to FIG. 17, the system 201 for characterizing select volumes of a material under test (MUT) 250 by performing processes described herein with respect to various embodiments is shown in greater detail. To this extent, the system 201 includes at least one computing device 204 that can perform one or more processes described herein in order to control operation of a sensor array system (e.g., electrode array 200, such as those shown and described with reference to FIGS. 7-11), a signal generator/comparator 203, and/or a input/output device 205. In particular, the system 201 is shown as including an MUT characterization system 223, which makes system 201 operable to characterize an MUT 250 (including a surface/subsurface) by performing any/all of the processes described herein and implementing any/all of the embodiments described herein. MUT characterization system 223 is further configured to utilize threshold data 221 and sensor data 220 to determine which layers of an MUT 250 are observed, and which electrode configurations (in array 200) can be used to obtain data about those layers of the MUT 250 in order to determine one or more physical properties of the MUT 250.

The computer device(s) 204 may provide alerts 216 to the user 212 via an audio or visual signal that may be transmitted through the input/output device 205 to advise of some condition that is identified by the computing device 204 that requires the user's 212 attention.

The system 201 is shown including the computing device 204, which can include a processing component 207 (e.g., one or more processors), a storage component 206 (e.g., a storage hierarchy), an input/output (I/O) component 208 (e.g., one or more I/O interfaces and/or devices), and a communications pathway 210. In general, the processing component 207 executes program code, such as the MUT characterization system 223, which is at least partially fixed in the storage component 206. While executing program code, the processing component 207 can process data, which can result in reading and/or writing transformed data from/to storage component 206 and/or I/O component 208 for further processing. The pathway 210 provides a communications link between each of the components in the computer system 204. I/O component 208 can comprise or be coupled with one or more human I/O devices 205, which enable a user (e.g., a human and/or computerized user) 212 to interact with the computer device 204 and/or one or more communications devices to enable the system user 212 to communicate with the computer device 204 using any type of communications link. To this extent, the MUT characterization system 223 can manage a set of interfaces (e.g., graphical user interface(s), application program interface, etc.) that enable human and/or system users 212 to interact with the MUT characterization system 223. Further, the MUT characterization system 223 can manage (e.g., store, retrieve, create, manipulate, organize, present, etc.) data, such as sensor data 220 and/or threshold data 221 using any solution. It is understood that the sensor data 220 can include data obtained by the sensor array 200 about the MUT 250. Threshold data 221 can include data representing one or more thresholds used to select sub-voxels for which a characteristic of the MUT 250 is determined. That is, the threshold data 221 can be based upon predetermined conditions which account for a threshold level of tomographic evaluation of the computed impedance values of the sub-voxels as described above. MUT characterization system 223 can additionally communicate with the electrode array 200, signal generator/analyzer 203, user 212 and/or input/output device 205, e.g., via wireless and/or hardwired means.

In any event, the computing device 204 can comprise one or more general purpose computing articles of manufacture (e.g., computing devices) capable of executing program code, such as MUT characterization system 223, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, MUT characterization system 223 can be embodied as any combination of system software and/or application software. It is further understood that the MUT characterization system 223 can be implemented in a cloud-based computing environment, where one or more processes are performed at distinct computing devices (e.g., a plurality of computing devices 204), where one or more of those distinct computing devices may contain only some of the components shown and described with respect to the computing device 204 of FIG. 17.

Further, the MUT characterization system 223 can be implemented using a set of modules 224. In this case, a module 224 can enable the computer device 204 to perform a set of tasks used by MUT characterization system 223, and can be separately developed and/or implemented apart from other portions of MUT characterization system 223. As used herein, the term "component" means any configuration of hardware, with or without software, which implements the functionality described in conjunction therewith using any solution, while the term "module" means program code that enables computer device 204 to implement the functionality described in conjunction therewith using any solution. When fixed in a storage component 206 of computer device 204 that includes a processing component 207, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computing device 204.

When the computer device 204 comprises multiple computing devices, each computing device may have only a portion of MUT characterization system 223 fixed thereon (e.g., one or more modules 224). However, it is understood that computing device 204 and MUT characterization system 223 are only representative of various possible equivalent computer systems that may perform a process described herein. To this extent, in other embodiments, the functionality provided by the computing device 204 and MUT characterization system 223 can be at least partially implemented by one or more computing devices that include any combination of general and/or specific purpose hardware with or without program code. In each embodiment, the hardware and program code, if included, can be created using standard engineering and programming techniques, respectively.

Regardless, when the computing device 204 includes multiple computing devices, the computing devices can communicate over any type of communications link. Further, while performing a process described herein, the computing device 204 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

Computing device 204 can obtain or provide data, such as sensor data 220 and/or threshold data 221 using any solution. Computing device 204 can compute sensor data 220 and/or threshold data 221, from one or more data stores, receive sensor data 220 and/or threshold data 221, from another system such as the electrode array 200, signal generator/analyzer 203, user 212 and/or display 205, send sensor data 220 and/or threshold optical data 221 to another system, etc.

While shown and described herein as a method and system for characterizing an MUT 250 (including, e.g., surface/subsurface layers) and determining which electrode configurations are preferable to detect impedance characteristics of portions of an MUT 250, it is understood that aspects of the invention further provide various alternative embodiments. For example, in one embodiment, the invention provides a computer program fixed in at least one computer-readable medium, which when executed, enables a computer system to detect and characterize at least a portion of an MUT 250. To this extent, the computer-readable medium includes program code, such as the MUT characterization system 223 (FIG. 17), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the MUT characterization system 223 (FIG. 17), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for characterizing an MUT 250. In this case, a computer system, such as the computing device 204 (FIG. 17), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the invention, including, e.g., the MUT characterization system 223, is to control operation of an electrode array 200, signal generator/analyzer 203, user 212 and/or input/output device 205 to characterize at least a portion of an MUT 250 in one of the various manners described and illustrated herein.

Figure 19:
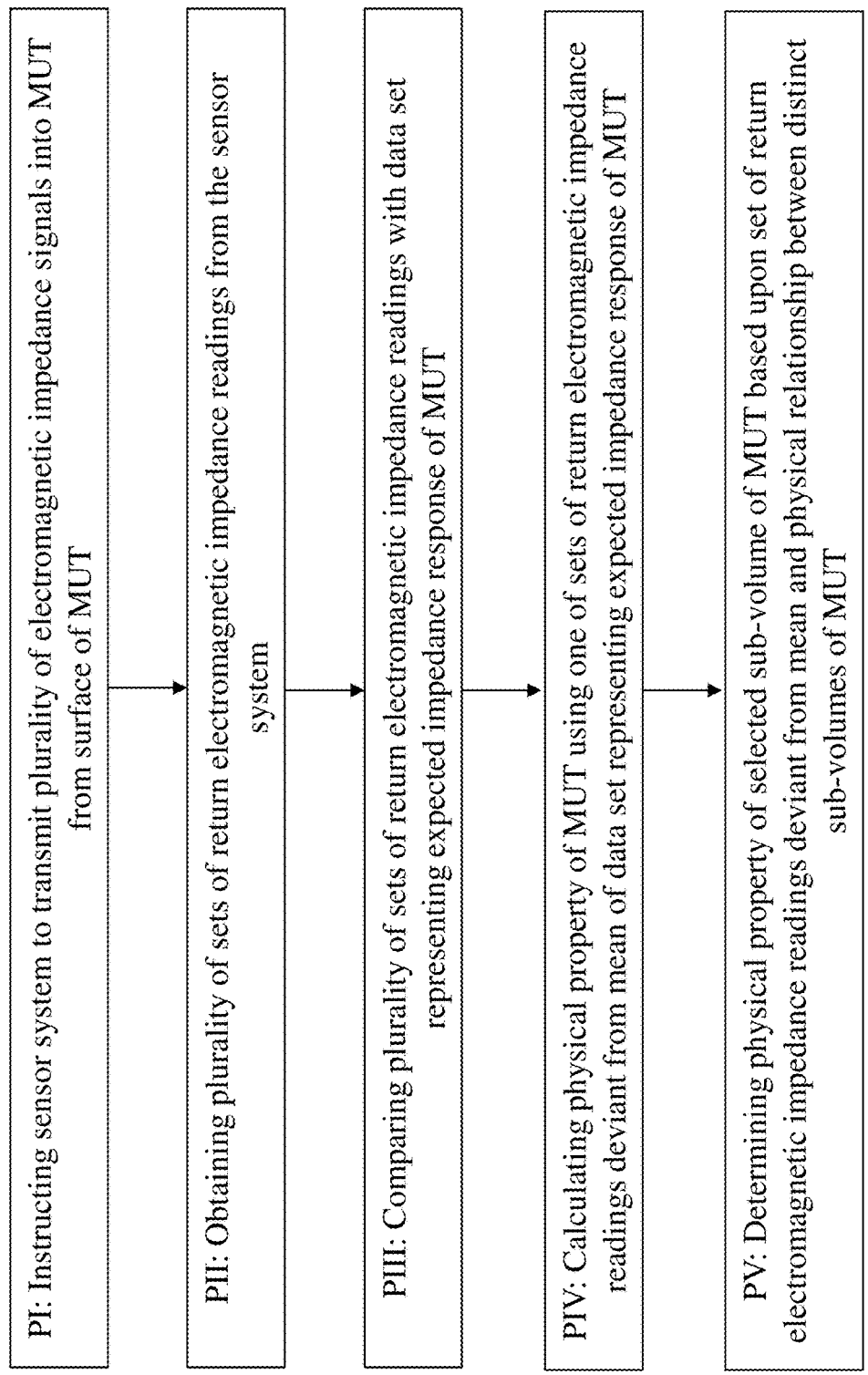
FIG. 19 shows a flow diagram illustrating a process according to various additional embodiments of the disclosure.

FIG. 19 shows an additional flow diagram illustrating processes of characterizing a physical property of an MUT 250, performed according to various embodiments of the disclosure. FIG. 19 is referred to in conjunction with various additional FIGURES herein, e.g., FIG. 17 and FIGS. 10-13. As shown, the process can include:

PI: Instructing a sensor system (e.g., electrode array 200) to transmit a plurality of electromagnetic impedance signals into MUT 250 from a surface of MUT 250. In some cases, this process includes instructing sensor system (e.g., electrode array 200) to transmit the plurality of electromagnetic impedance signals into MUT 250 and obtaining a first one of the plurality of sets of return electromagnetic impedance readings using a first configuration of the array of electrodes, and subsequently instructing the sensor system (e.g., electrode array 200) to transmit the plurality of electromagnetic impedance signals into MUT 250 and obtain a second one of the plurality of sets of return electromagnetic impedance readings using a second configuration of the array of electrodes, the second configuration being distinct from the first configuration.

PII: Obtaining a plurality of sets of return electromagnetic impedance readings from the sensor system (e.g., electrode array 200), including impedance information about MUT 250, the plurality of sets of return electromagnetic impedance readings each representing a subset of the plurality of electromagnetic impedance signals transmitted into MUT 250. This process can include obtaining impedance data about a plurality of voxels (e.g., voxels Axy, Bxy, etc.) within MUT 250;

PIII: Comparing each of the plurality of sets of return electromagnetic impedance readings with a data set representing an expected impedance response of the MUT 250. This can include determining which set(s) of electromagnetic impedance readings differ from the mean data set for that given MUT 250 (e.g., a data set of expected impedance responses for that particular type of MUT, such as human tissue, asphalt, sand, et.);

PIV: Calculating the physical property of MUT 250 using one of the plurality of sets of return electromagnetic impedance readings differing from a mean of the data set representing an expected impedance response of the MUT 250. This process can include selecting the data set(s) which have a greatest deviation from the mean of the expected impedance response data for a particular MUT 250. For example, when testing human tissue to determine characteristics of blood within that tissue, the data set representing the expected impedance response for the MUT 250 can include a data set having a mean that represents the approximate impedance of tissue, whereas the impedance of blood within that tissue will have a significantly different (e.g., greater) impedance. Where the data set received from the sensor system (e.g., array 203) differs from the mean by a significant measure (e.g., one or more standard deviations from the mean), that data set may be assumed to characterize blood within the tissue. That is, the electrodes which penetrate that area of the MUT 250 can provide valuable information about the blood in that region (e.g., within a given voxel or sub-voxel); and PV: Determining the physical property of a selected sub-volume of the MUT 250 based upon the set of return electromagnetic impedance readings differing from the mean and a physical relationship between distinct sub-volumes of the MUT 250. This process can include comparing the impedance readings from particular electrode combinations which penetrate voxels or sub-voxels of interest with threshold data 221 (FIG. 17) to determine characteristics about the MUT 250 in those regions. In some cases, this process can include calculating impedance characteristics about voxels and/or sub-voxels not directly measured by a set of electrodes, but where the impedance values may be calculated based upon at least one of a series or parallel circuit calculation using known physical relationships (e.g., depth, spacing, etc.) between a measured voxel or sub-voxel (volumes/sub-volumes) and a voxel or sub-voxel not directly measured. In some cases, the distinct volume (voxels) or sub-volumes (sub-voxels) can be located within a same layer (depth) within MUT 250 as measured from the surface, and in other cases, the distinct volumes/sub-volumes can be located at distinct depths within MUT 250.

In additional embodiments, a method of selecting volumes of an MUT 250 using electromagnetic impedance tomography and applying spectroscopy to characterize physical properties of the selected volume, includes:

A) obtaining the tomographic complex electromagnetic impedance of volumes or voxels of MUT 250 with a linear or planar array of electrodes with various patterns of a four-terminal electrode measurement at a single frequency;

B) computing the tomographic impedance values of the subsurface sub-voxels by the application of circuit theory from the measured impedance values of the voxels;

C) selecting the tomographic impedance value of a sub-voxel by apply a statistical methodology to select a sub-voxel's computed tomographic impedance characteristic is statistically greater than the mean value;

D) identifying and selecting the electrode pattern associated with the selected sub-voxel;

E) obtaining the complex electromagnetic impedance over a range of frequencies with various electrode patterns that includes the selected electrode pattern to secure adequate data to be able to apply tomographic and spectrographic methods;

F) computing the spectrographic impedance values of the subsurface sub-voxels by the application of circuit theory from the measured impedance values of the voxels; and G) correlating the spectrographic impedance of the subsurface sub-voxels to a desired physical property of MUT 250.

In some cases, the four-terminal electrode measurement consists of two electrodes inserting an oscillating current into MUT 250 and two electrodes measuring the induced voltage in MUT 250. In additional embodiments the four-terminal electrode measurement consists of the two voltage measuring electrodes being within the two current inserting electrodes. According to various embodiments, the center-to-center distance of the electrodes of the four-terminal electrode measurement pattern is equal.

In other cases, the center-to center distance of the four-terminal electrode pattern which measures the thinnest layer of MUT 250 is equal to the thickness, A, of that layer.

According to some embodiments, the number of four-terminal electrode patterns is equal to the number of layers, n, of MUT 250 to be characterized. In these cases, the center-to-center spacing of the electrodes in each of the four-terminal electrode patterns can be an integer multiple of spacing for the thinnest layer, $\Delta$.

In various embodiments, the electrode array is linear or planar. In some particular cases, the minimum number of electrodes in a linear array for the four-terminal electrode patterns to measure n layers is equal to 3n+1.

According to some embodiments, the statistical method for selecting the tomographic impedance value of a sub-voxel includes the computation of the standard deviation of all the computed impedance characteristic of the sub-voxels, excluding the first layer, and selecting the sub voxel with the largest standard deviation that results in a value larger than the mean. In these cases, selection of the sub-voxel(s) can be based on the selection of those sub-voxel(s) whose computed impedance characteristic is at least N times the standard deviation larger than the mean, where N is greater than 2. In particular cases, the value of N can be equal to 3.

As described herein, in various embodiments, a system can include: an array of electrodes for communicating with a surface and a subsurface beneath the surface; a four-terminal electrode pattern within the array of electrodes consisting of two current transmitting electrodes and two voltage sensing electrodes; a current generator operably connected with the array of electrodes; a voltage sensor operably connected with the array of electrodes; and at least one computing device operably connected with the current generator, the voltage sensor, and the array of electrodes, the at least one computing device configured to:

Pi) instruct the current generator to transmit a tomographic signal at a single frequency to the current electrodes of a first set of four-terminal electrode patterns into the surface and the subsurface;

Pii) obtain a voltage signal from the voltage electrodes of the four-terminal electrode pattern;

Piii) instruct the current generator to transmit tomographic signals at the same single frequency to the current electrodes of all of the remaining sets of four-terminal electrode patterns into the surface and subsurface;

Piv) obtain voltage signals from the voltage electrodes of all of the remaining sets of four-terminal electrode patterns;

Pv) compute the voxel and sub-voxel tomographic electromagnetic impedance;

Pvi) select the sub-voxels with the target impedance value and identify the four-terminal electrode pattern coinciding with that measurement;

Pvii) instruct the current generator to transmit a spectrographic signal over a range of frequencies to the current electrodes of the selected four-terminal electrode pattern and the related patterns required for a tomographic analysis of the voxels and sub-voxels with the target impedance of the surface and the subsurface;

Pviii) obtain a voltage signal from the voltage electrodes of selected four-terminal electrode pattern and the related patterns required for a tomographic analysis of the voxels and sub-voxels with the target impedance of the surface and the subsurface;

Pix) compute the voxel and sub-voxel tomographic electromagnetic impedance for each frequency in the range of frequencies;

Px) compute the spectrographic electromagnetic impedance for the sub-voxel with the target impedance; and Pxi) correlate the computed spectrographic electromagnetic impedance with the desired physical property of MUT.

In some cases, as noted herein, the four-terminal electrode measurement consists of two electrodes inserting an oscillating current into MUT 250 and two electrodes measuring the induced voltage in MUT 250. In particular cases the four-terminal electrode measurement consists of the two voltage measuring electrodes being within the two current inserting electrodes.

Additional embodiments can include a computer program product having program code stored on a computer readable storage medium, which when executed by at least one computing device coupled to a current generator, a voltage sensor, and an array of electrodes, causes the at least one computing device to execute a method of correlating the computed electromagnetic impedance of a select volume to a physical property of a material under test (MUT) 250 by performing actions including:

a) instructing the current generator to transmit a tomographic signal at a single frequency to the current electrodes of a first set of four-terminal electrode patterns into the surface and the subsurface;

b) obtaining a voltage signal from the voltage electrodes of the four-terminal electrode pattern;

c) instructing the current generator to transmit tomographic signals at the same single frequency to the current electrodes of all of the remaining sets of four-terminal electrode patterns into the surface and subsurface;

d) obtaining voltage signals from the voltage electrodes of all of the remaining sets of four-terminal electrode patterns;

e) computing the voxel and sub-voxel tomographic electromagnetic impedance;

f) selecting the sub-voxels with the target impedance value and identify the four-terminal electrode pattern coinciding with that measurement;

g) instructing the current generator to transmit a spectrographic signal over a range of frequencies to the current electrodes of the selected four-terminal electrode pattern and the related patterns required for a tomographic analysis of the voxels and sub-voxels with the target impedance of the surface and the subsurface;

h) obtaining a voltage signal from the voltage electrodes of selected four-terminal electrode pattern and the related patterns required for a tomographic analysis of the voxels and sub-voxels with the target impedance of the surface and the subsurface;

i) computing the voxel and sub-voxel tomographic electromagnetic impedance for each frequency in the range of frequencies;

j) computing the spectrographic electromagnetic impedance for the sub-voxel with the target impedance; and k) correlating the computed spectrographic electromagnetic impedance with the desired physical property of MUT 250.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
    at least one computing device configured to characterize a physical property of a material under test (MUT) by performing actions including:
        instructing a sensor system coupled with the at least one computing device to transmit a plurality of electromagnetic impedance signals into the MUT from a surface of the MUT, wherein the sensor system comprises an array of electrodes;
        obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT;
        comparing each of the plurality of sets of return electromagnetic impedance readings with a data set representing an expected impedance response of the MUT;
        identifying at least one of the plurality of sets of return electromagnetic impedance readings that differs from a mean of the data set representing an expected impedance response of the MUT by at least one standard deviation; and
        determining the physical property of a selected sub-volume of the MUT using only the at least one set of return electromagnetic impedance readings that differs from the mean by at least one standard deviation and a physical relationship between distinct sub-volumes of the MUT,
        wherein instructing the sensor system to transmit the plurality of electromagnetic impedance signals into the MUT includes:
            instructing the sensor system to transmit the plurality of electromagnetic impedance signals into the MUT and obtain a first one of the plurality of sets of return electromagnetic impedance readings using a first configuration of the array of electrodes; and
            instructing the sensor system to transmit the plurality of electromagnetic impedance signals into the MUT and obtain a second one of the plurality of sets of return electromagnetic impedance readings using a second configuration of the array of electrodes, the second configuration being distinct from the first configuration, wherein the second configuration of the array of electrodes comprises a subset of the first configuration of the array of electrodes, and wherein the second configuration of the array of electrodes is selected to characterize the selected sub-volume based upon a correlation of the second configuration of the array of electrodes with the at least one of the plurality of sets of return electromagnetic impedance readings deviating from the mean of the data set by at least one standard deviation.

2. The system of claim 1, wherein the determining of the physical property of the selected sub-volume of the MUT is performed using at least one of a series circuit equation or a parallel circuit equation using the set of return electromagnetic impedance readings differing from the mean and the physical relationship between distinct sub-volumes of the MUT.

3. A computer-implemented method of characterizing a physical property of a material under test (MUT), performed using at least one computing device, the method comprising:
    instructing a sensor system to transmit a plurality of electromagnetic impedance signals into the MUT from a surface of the MUT, wherein the sensor system comprises an array of electrodes;

obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT;

comparing each of the plurality of sets of return electromagnetic impedance readings with a data set representing an expected impedance response of the MUT;

identifying at least one of the plurality of sets of return electromagnetic impedance readings that differs from a mean of the data set representing an expected impedance response of the MUT by at least one standard deviation; and determining the physical property of a selected sub-volume of the MUT using only the at least one set of return electromagnetic impedance readings that differs from the mean by at least one standard deviation and a physical relationship between distinct sub-volumes of the MUT, wherein instructing the sensor system to transmit the plurality of electromagnetic impedance signals into the MUT includes:

instructing the sensor system to transmit the plurality of electromagnetic impedance signals into the MUT and obtain a first one of the plurality of sets of return electromagnetic impedance readings using a first configuration of the array of electrodes; and instructing the sensor system to transmit the plurality of electromagnetic impedance signals into the MUT and obtain a second one of the plurality of sets of return electromagnetic impedance readings using a second configuration of the array of electrodes, the second configuration being distinct from the first configuration, wherein the second configuration of the array of electrodes comprises a subset of the first configuration of the array of electrodes, and wherein the second configuration of the array of electrodes is selected to characterize the selected sub-volume based upon a correlation of the second configuration of the array of electrodes with the at least one of the plurality of sets of return electromagnetic impedance readings deviating from the mean of the data set by at least one standard deviation.

4. The method of claim 3, wherein the determining of the physical property of the selected sub-volume of the MUT is performed using at least one of a series circuit equation or a parallel circuit equation using the set of return electromagnetic impedance readings differing from the mean and the physical relationship between distinct sub-volumes of the MUT.

5. A computer program product comprising program code stored on a non-transitory computer-readable storage medium, which when executed by at least one computing device, causes the at least one computing device to characterize a physical property of a material under test (MUT) by performing actions including: instructing a sensor system to transmit a plurality of electromagnetic impedance signals into the MUT from a surface of the MUT, wherein the sensor system comprises an array of electrodes;

obtaining a plurality of sets of return electromagnetic impedance readings from the sensor system, including impedance information about the MUT, the plurality of sets of return electromagnetic impedance readings each representing a subset of the plurality of electromagnetic impedance signals transmitted into the MUT;

comparing each of the plurality of sets of return electromagnetic impedance readings with a data set representing an expected impedance response of the MUT;

identifying at least one of the plurality of sets of return electromagnetic impedance readings that differs from a mean of the data set representing an expected impedance response of the MUT by at least one standard deviation; and determining the physical property of a selected sub-volume of the MUT using only the at least one set of return electromagnetic impedance readings that differs from the mean by at least one standard deviation and a physical relationship between distinct sub-volumes of the MUT, wherein instructing the sensor system to transmit the plurality of electromagnetic impedance signals into the MUT includes:

instructing the sensor system to transmit the plurality of electromagnetic impedance signals into the MUT and obtain a first one of the plurality of sets of return electromagnetic impedance readings using a first configuration of the array of electrodes; and instructing the sensor system to transmit the plurality of electromagnetic impedance signals into the MUT and obtain a second one of the plurality of sets of return electromagnetic impedance readings using a second configuration of the array of electrodes, the second configuration being distinct from the first configuration, wherein the second configuration of the array of electrodes comprises a subset of the first configuration of the array of electrodes, and wherein the second configuration of the array of electrodes is selected to characterize the selected sub-volume based upon a correlation of the second configuration of the array of electrodes with the at least one of the plurality of sets of return electromagnetic impedance readings deviating from the mean of the dataset by at least one standard deviation.

6. The computer program product of claim 5, wherein the determining of the physical property of the selected sub-volume of the MUT is performed using at least one of a series circuit equation or a parallel circuit equation using the set of return electromagnetic impedance readings differing from the mean and the physical relationship between distinct sub-volumes of the MUT.

7. The computer program product of claim 6, wherein the distinct sub-volumes of the MUT are located at approximately a same depth within the MUT, measured from the surface of the MUT.

8. The computer program product of claim 6, wherein the distinct sub-volumes of the MUT are located at distinct depths within the MUT, measured from the surface of the MUT.

* * * * *